United States Patent
Nordvall et al.

(10) Patent No.: US 9,822,075 B2
(45) Date of Patent: Nov. 21, 2017

(54) NMDA ANTAGONIST PRODRUGS

(71) Applicant: AstraZeneca AB, Södertälje (SE)

(72) Inventors: Gunnar Nordvall, Rönninge (SE); Katharina Hogdin, Knivsta (SE); Per Jonas Malmborg, Linköping (SE); Annika Kers, Malmö (SE); Dirk Reinhold Weigelt, Rönninge (SE); Peter Robert Bernstein, Rose Valley, PA (US); Michael Quirk, Acton, MA (US); Michael Balestra, New Fairfield, CT (US)

(73) Assignee: AstraZeneca AB, Södertälje (SE)

(*) Notice: Subject to any disclaimer, the term of this patent is extended or adjusted under 35 U.S.C. 154(b) by 13 days.

(21) Appl. No.: 15/034,727

(22) PCT Filed: Oct. 30, 2014

(86) PCT No.: PCT/GB2014/053236
§ 371 (c)(1),
(2) Date: May 5, 2016

(87) PCT Pub. No.: WO2015/067923
PCT Pub. Date: May 14, 2015

(65) Prior Publication Data
US 2016/0280647 A1    Sep. 29, 2016

Related U.S. Application Data

(60) Provisional application No. 61/899,903, filed on Nov. 5, 2013.

(51) Int. Cl.
| | | |
|---|---|---|
| *A61K 38/00* | (2006.01) | |
| *C07K 5/078* | (2006.01) | |
| *C07D 401/12* | (2006.01) | |
| *C07D 213/40* | (2006.01) | |
| *C07D 401/14* | (2006.01) | |
| *C07K 5/062* | (2006.01) | |
| *C07K 5/065* | (2006.01) | |
| *C07K 5/072* | (2006.01) | |

(52) U.S. Cl.
CPC .......... *C07D 213/40* (2013.01); *C07D 401/12* (2013.01); *C07D 401/14* (2013.01); *C07K 5/06043* (2013.01); *C07K 5/06078* (2013.01); *C07K 5/06095* (2013.01); *C07K 5/06104* (2013.01); *C07K 5/06139* (2013.01); *C07K 5/06147* (2013.01); *A61K 38/00* (2013.01)

(58) Field of Classification Search
None
See application file for complete search history.

(56) References Cited

U.S. PATENT DOCUMENTS

| | | |
|---|---|---|
| 6,479,553 B1 | 11/2002 | McCarthy |
| 7,227,028 B2 | 6/2007 | Gallop et al. |
| 7,511,158 B2 | 3/2009 | Gallop et al. |
| 8,003,809 B2 | 8/2011 | Gallop et al. |
| 8,062,870 B2 | 11/2011 | Gallop et al. |
| 8,299,291 B2 | 10/2012 | Raillard et al. |
| 8,378,137 B2 | 2/2013 | Gallop et al. |

FOREIGN PATENT DOCUMENTS

| | | |
|---|---|---|
| EP | 14802476.3 | 3/2017 |
| WO | WO9320052 | 10/1993 |
| WO | WO0056324 | 9/2000 |
| WO | WO0063175 | 10/2000 |
| WO | WO0071571 | 11/2000 |
| WO | WO0216321 | 2/2002 |
| WO | WO2010017504 | 2/2010 |
| WO | WO2011089216 | 7/2011 |
| WO | WO2015067923 | 1/2015 |
| WO | WO2015067923 | 5/2016 |

OTHER PUBLICATIONS

Mittal 2005 "prolidase, a potential enzyme target for melanoma: design of proline-containing dipeptide-like prodrugs" Mol Pharma 2(1):37-46.*
Sancora, Adjunctive AZD6765, a Low-trapping NMDA Channel Blocker, in Treatment-resistant Major Depressive Disorder: A Randomized, Placebocontrolled Study, Poster Session II, No. 28, ACNP 2012 51st Annual Meeting Program, p. 242, USA.
Haradahira, A Prodrug of NMDA/Glycine Site Antagonist, L-703,717, with Improved BBB Permeability: 4-Acetoxy Derivative and Its Positron-Emitter Labeled Analog, Chem. Pharm. Bull. 49(2) 147-150 (2001), Japan.
Rautio, Prodrugs: design and clinical applications, Nature Reviews Drug Discovery—Apr. 2008, GB.
Sanacora, Lanicemine: a low-trapping NMDA channel blocker produces sustained antidepressant efficacy with minimal psychotomimetic adverse effects, Molecular Psychiatry (2014) 19, 978-985, GB.

\* cited by examiner

*Primary Examiner* — Adam M Weidner

(57) ABSTRACT

Prodrugs of an NMDA antagonist, (S)-1-phenyl-2-(pyridin-2-yl)ethanamine, useful for the treatment of depression (particularly major depressive disorder) or pain; compositions comprising them, and methods of making them.

12 Claims, 1 Drawing Sheet

NMDA ANTAGONIST PRODRUGS

CROSS-REFERENCE TO RELATED APPLICATIONS

This application is a national stage application under 35 U.S.C. §371 of International Application No. PCT/GB2014/053236, filed Oct. 30, 2014, which claims the benefit of priority to U.S. provisional patent application Ser. No. 61/899,903, filed Nov. 5, 2013, the entire disclosure of each of which is incorporated herein by reference.

This invention is directed to prodrugs of an NMDA antagonist, (S)-1-phenyl-2-(pyridin-2-yl)ethanamine, and their use in the treatment of depression and depressive disorders, particularly major depressive disorder (MDD), and also for the treatment of pain (such as neuropathic pain). The prodrugs of (S)-1-phenyl-2-(pyridin-2-yl)ethanamine can also be used to treat Rett Syndrome, suicidal ideation, bipolar disorder (including bipolar depression), obsessive compulsive disorder, sarin gas poisoning, and status epilepticus. The invention also relates to pharmaceutical compositions comprising the prodrugs and to processes for preparing them.

Pain in one form or another is a pervasive part of human life. Pain from injury and post-surgical pain is often temporary, but can be severe, and can persist. Neuropathic pain such as diabetic neuropathy and post-herpetic neuralgia severely impacts sufferers. Every year, tens of millions of people around the world, including patients at the end of their lives, suffer from pain without adequate treatment.

Depression affects about 120 million people worldwide. Symptoms of depression include, but are not limited to, depressed mood, loss of interest or pleasure, feelings of guilt or low self-worth, disturbed sleep or appetite, low energy, and poor concentration, or any combination thereof. These problems can be chronic or recurrent and can lead to substantial impairment of an individual's ability to take care of his or her everyday responsibilities. Depression is the leading cause of disability as measured by Years Lived with a Disability (YLDs) and the fourth leading contributor to the global burden of disease as measured by Disability Adjusted Life Years (DALYs; i.e., the sum of years of potential life lost due to premature mortality and the years of productive life lost due to disability) in 2000. By the year 2020, depression is projected to reach second place in the ranking of DALYs calculated for all ages, in both men and women. Today, depression is already the second cause of DALYs in the age category 15-44 years for both sexes combined.

(S)-1-Phenyl-2-(pyridin-2-yl)ethanamine dihydrochloride has been disclosed for the treatment of MDD via intravenous infusion treatment (Gerard Sanacora et al, poster presented on 6 Dec. 2012 at the 51st Annual Meeting of the American College of Neuropsychopharmacology in Hollywood, Fla., USA. Other related disclosures include WO1993/020052, WO2000/056324, and WO2000/63175. For convenience it would be useful to be able to administer this drug as an oral dosage form. However, a concern with such an oral dosage form of (S)-1-phenyl-2-(pyridin-2-yl)ethanamine dihydrochloride would be that it would be open to misuse intravenously, for example, tablet crushing of an oral dosage form of (S)-1-phenyl-2-(pyridin-2-yl)ethanamine dihydrochloride followed by immediate injection of the resulting crushed oral dosage form of (S)-1-phenyl-2-(pyridin-2-yl)ethanamine dihydrochloride. Prodrugs of (S)-1-phenyl-2-(pyridin-2-yl)ethanamine are predicted to break down in a human body to provide (S)-1-phenyl-2-(pyridin-2-yl)ethanamine, so that, when prodrugs of (S)-1-phenyl-2-(pyridin-2-yl)ethanamine are administered orally, they would break down to liberate a therapeutically effective dose of (S)-1-phenyl-2-(pyridin-2-yl)ethanamine. But if a prodrug of the present invention is administered intravenously it is predicted that the prodrug would liberate (S)-1-phenyl-2-(pyridin-2-yl)ethanamine to give a lower Cmax, at a slower rate, than if the corresponding dose of (S)-1-phenyl-2-(pyridin-2-yl)ethanamine had been administered intravenously. The use of prodrugs of (S)-1-Phenyl-2-(pyridin-2-yl)ethanamine would be predicted to improve the clinical safety profile of (S)-1-Phenyl-2-(pyridin-2-yl)ethanamine (for example under overdose or, drug abuse (eg pill crushing) conditions). Thus, in summary, putting (S)-1-phenyl-2-(pyridin-2-yl)ethamamine directly into an oral formulation could lead to abuses. Compounds of the present invention metabolise in vivo to give (S)-1-phenyl-2-(pyridin-2-yl)ethamamine, but at a slower rate than the rate when (S)-1-phenyl-2-(pyridin-2-yl)ethanamine is administered intravenously, and therefore would not encourage potential abuse of (S)-1-phenyl-2-(pyridin-2-yl)ethanamine.

DESCRIPTION OF THE DRAWINGS

FIG. 1a illustrates prodrug of (S)-1-phenyl-2-(pyridin-2-yl)ethanamine (Example 5) concentration (initial concentrations of 30, 100, 300 and 600 μM), as it transforms to (S)-1-phenyl-2-(pyridin-2-yl)ethanamine, during an incubation period in human intestinal fluid. FIG. 1b illustrates (S)-1-phenyl-2-(pyridin-2-yl)ethanamine concentration, as it converts from prodrug of (S)-1-phenyl-2-(pyridin-2-yl)ethanamine (Example 5, initial concentrations of 30, 100, 300 and 600 μM), during an incubation period in human intestinal fluid.

SUMMARY OF THE INVENTION

Figure 1A:
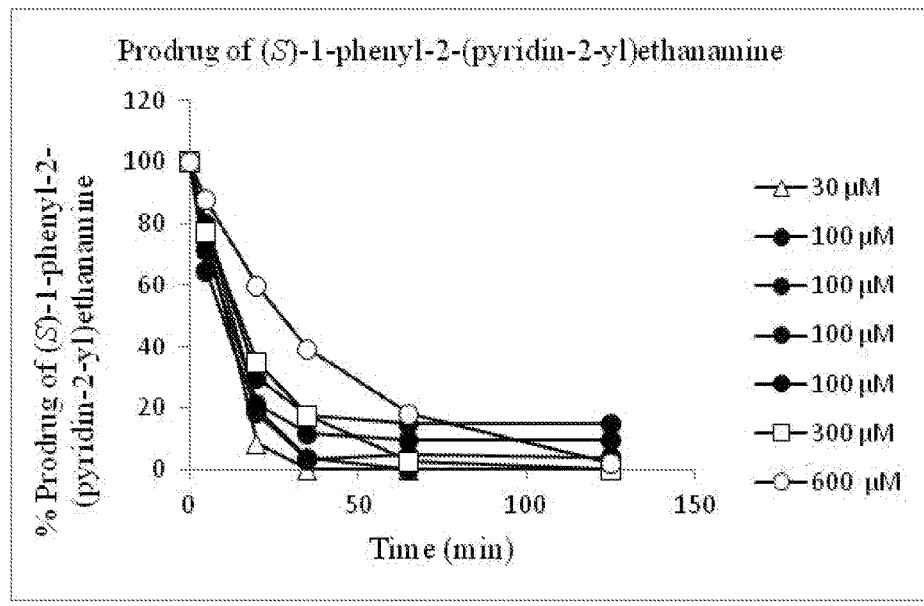
FIGS. 1a and 1b illustrates the conversion of prodrug of (S)-1-phenyl-2-(pyridin-2-yl)ethanamine (Example 5) to (S)-1-phenyl-2-(pyridin-2-yl)ethanamine during an incubation period in human intestinal fluid. In particular.

The present invention provides a compound of formula (I):

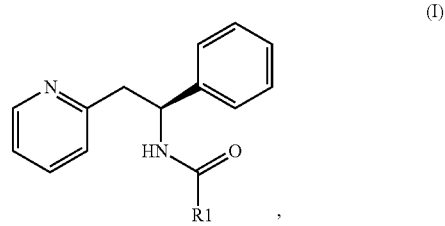

(I)

wherein R1 is $C_{1-6}$ alkylC(O)O($C_{1-6}$alkoxy), or

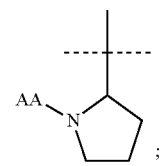

AA is a peptide bond-linked natural amino acid;
or a pharmaceutically acceptable salt thereof.

Alkyl is straight or branched chain and contains 1-6, for example 1-4, carbon atoms. Alkyl is, for example, methyl, ethyl, n-propyl, iso-propyl, n-butyl, sec-butyl, iso-butyl or tert-butyl.

Alkoxy is straight or branched chain and contain 1-6, for example 1-4, carbon atoms. Alkoxy is, for example, methoxy, ethoxy, n-propoxy, iso-propoxy, n-butoxy, sec-butoxy, iso-butoxy or tert-butoxy.

DETAILED DESCRIPTION OF THE INVENTION

In one aspect the present invention provides a compound of formula (I) wherein R1 is $C_{1-6}$ alkylC(O)O($C_{1-6}$alkoxy), for example it is $C_{1-4}$ alkylC(O)O($C_{1-4}$ alkoxy). Examples include: $(CH_3)_2CHC(O)OCH_2O$, $(CH_3)_2CHC(O)OCH(CH(CH_3)_2)O$, $CH_3C(O)OCH(CH_3)O$ or $(CH_3)_2CHC(O)OCH(CH_3)O$.

In another aspect the present invention provides a compound of formula (I) wherein R1 is

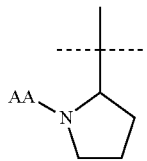

and AA is a peptide bond-linked natural amino acid.

In yet another aspect the present invention provides a compound of formula (I) wherein R1 is

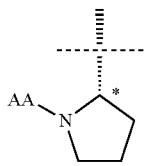

(so the chiral centre * has S absolute configuration).

In a further aspect the present invention provides a compound of formula (I) wherein AA is, for example, glycine, alanine, valine, leucine, isoleucine, serine, threonine, cysteine, cystine, methionine, aspartic acid, glutamic acid, asparagine, glutamine, lysine, hydroxylysine, arginine, histidine, phenylalanine, tyrosine, tryptophan, proline or hydroxyproline. In a still further aspect AA is selected from the group consisting of tyrosine, tryptophan, phenylalanine, leucine, arginine, histidine, lysine and valine. In another aspect AA is selected from the group consisting of tyrosine, arginine, histidine, lysine and valine. In a still further aspect AA is valine.

A suitable pharmaceutically acceptable salt is, for example, an acid addition salt such as a hydrochloride, hydrobromide, sulphate, phosphate, acetate, fumarate, maleate, tartrate, lactate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, L-lactate, D-lactate, aspartate, malate, L-tartrate, D-tartrate, stearate, 2-furoate, 3-furoate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), 2-mesitylenesulphonate, 2-naphthalenesulphonate, D-mandelate, L-mandelate, 2,5-dichlorobenzenesulphonate, cinnamate or benzoate.

A compound of formula (I) which is:
(S)-(1-Phenyl-2-(pyridin-2-yl)ethylcarbamoyloxy)methyl isobutyrate;
2-Methyl-1-((S)-1-phenyl-2-(pyridin-2-yl)ethylcarbamoyloxy)propyl isobutyrate;
2-Methyl-1-((S)-1-phenyl-2-(pyridin-2-yl)ethylcarbamoyloxy)propyl isobutyrate diastereomer 1;
2-Methyl-1-((S)-1-phenyl-2-(pyridin-2-yl)ethylcarbamoyloxy)propyl isobutyrate diastereomer 2;
1-((S)-1-phenyl-2-(pyridin-2-yl)ethylcarbamoyloxy)ethyl acetate;
1-((S)-1-phenyl-2-(pyridin-2-yl)ethylcarbamoyloxy)ethyl acetate diastereomer 1;
1-((S)-1-phenyl-2-(pyridin-2-yl)ethylcarbamoyloxy)ethyl acetate diastereomer 2;
1-((S)-1-Phenyl-2-(pyridin-2-yl)ethylcarbamoyloxy)ethyl isobutyrate;
1-((S)-1-Phenyl-2-(pyridin-2-yl)ethylcarbamoyloxy)ethyl isobutyrate diastereomer 1;
1-((S)-1-Phenyl-2-(pyridin-2-yl)ethylcarbamoyloxy)ethyl isobutyrate diastereomer 2;
(S)-1-((S)-2-Amino-3-methylbutanoyl)-N—((S)-1-phenyl-2-(pyridin-2-yl)ethyl)pyrrolidine-2-carboxamide;
(S)-1-((S)-2,6-Diaminohexanoyl)-N—((S)-1-phenyl-2-(pyridin-2-yl)ethyl)pyrrolidine-2-carboxamide;
(S)-1-((S)-2-Amino-3-(1H-imidazol-4-yl)propanoyl)-N—((S)-1-phenyl-2-(pyridin-2-yl)ethyl)pyrrolidine-2-carboxamide;
2-((S)-2-((S)-1-((S)-2-Amino-3-(4-hydroxyphenyl)propanoyl)pyrrolidine-2-carboxamido)-2-phenylethyl)pyridine;
2-((S)-2-((S)-1-((S)-2-Amino-3-(1H-indol-3-yl)propanoyl)pyrrolidine-2-carboxamido)-2-phenylethyl)pyridine;
(S)-1-((S)-2-Amino-3-phenylpropanoyl)-N—((S)-1-phenyl-2-(pyridin-2-yl)ethyl)pyrrolidine-2-carboxamide; or,
(S)-1-((S)-2-Amino-4-methylpentanoyl)-N—((S)-1-phenyl-2-(pyridin-2-yl)ethyl)pyrrolidine-2-carboxamide;
or a pharmaceutically acceptable salt of any one of the foregoing.

Compounds of the invention can be prepared by adapting methods described in the art or by adapting methods described in the Examples. The compound (S)-1-phenyl-2-(pyridin-2-yl)ethanamine) can be prepared, for example, by process methodology in EP-0633879 and the content of that document is incorporate by reference.

Compounds of the present invention wherein R1 is

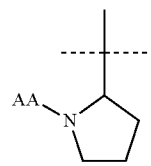

can be synthesized using a chemical process that proceeds though a 2-((S)-2-phenyl-2-((S)-pyrrolid-2-incarboxamido)ethyl)pyridine intermediate.

Thus, in another aspect, the present invention provides the compound 2-((S)-2-phenyl-2-((S)-pyrrolid-2-incarboxamido)ethyl)pyridine:

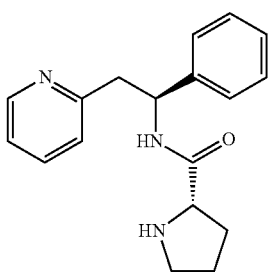 [SMILES: O=C(N[C@@H](Cc1ccccn1)c1ccccc1)[C@@H]1CCCN1]

or a salt thereof, wherein said salt is, for example, a hydrochloride, hydrobromide, sulphate, phosphate, acetate, methanesulphonate, p-toluenesulphonate, formate or benzoate salt.

In a further aspect the present invention provides the intermediate compound 2-((S)-2-phenyl-2-((S)-pyrrolidin-2-iumcarboxamido)ethyl)pyridinium chloride

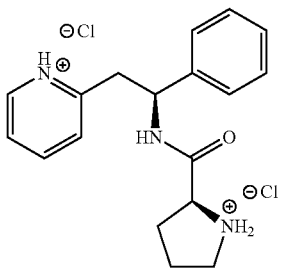

A compound of formula (I), or a pharmaceutically acceptable salt thereof, can be used in the treatment of depression (such as major depressive disorder, for example treatment resistant major depressive disorder).

A compound of formula (I), or a pharmaceutically acceptable salt thereof, can be used in the treatment of pain (such as neuropathic pain, chronic pain, phantom-limb pain, nociceptive pain, psychogenic pain, incident pain or breakthrough pain).

A compound of formula (I), or a pharmaceutically acceptable salt thereof, can be used in the treatment of Rett Syndrome, suicidal ideation, bipolar disorder, obsessive compulsive disorder, sarin gas poisoning, or status epilepticus.

Thus, the present invention provides a compound of formula (I) or a pharmaceutically-acceptable salt thereof as defined herein for use in therapy. Therefore, the term "prodrug" as used herein may refer to a compound of formula (I) in the form of a salt or in the form of a free base.

In a further aspect, the present invention provides the use of a compound of formula (I) or a pharmaceutically acceptable salt thereof as defined herein in the manufacture of a medicament for use in therapy.

In a further aspect the present invention provides a method of administering (S)-1-phenyl-2-(pyridin-2-yl)ethanamine to a patient, said method comprising administering a compound of formula (I), of a pharmaceutically acceptable salt thereof, to a patient wherein said compound of formula (I) metabolises in said patient to produce (S)-1-phenyl-2-(pyridin-2-yl)ethanamine.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention still further provides a method of treating depression which comprises administering to a patient in need thereof a therapeutically effective amount of a compound of formula (I) or a pharmaceutically acceptable salt thereof as defined herein.

The invention still further provides a method of treating MDD which comprises administering to a patient in need thereof a therapeutically effective amount of a compound of formula (I) or a pharmaceutically acceptable salt thereof as defined herein.

The invention still further provides a method of treating pain which comprises administering to a patient in need thereof a therapeutically effective amount of a compound of formula (I) or a pharmaceutically acceptable salt thereof as defined herein.

The invention still further provides a method of treating neuropathic pain, chronic pain, phantom-limb pain, nociceptive pain, psychogenic pain, incident pain or breakthrough pain which comprises administering to a patient in need thereof a therapeutically effective amount of a compound of formula (I) or a pharmaceutically acceptable salt thereof as defined herein.

The use of a compound of formula (I) or a pharmaceutically acceptable salt thereof for the treatment of depression.

The use of a compound of formula (I) or a pharmaceutically acceptable salt thereof for the treatment of pain.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (µg/kg) to 100 micrograms per kilogram body weight (µg/kg). Alternatively, if the compound is administered orally, then the daily dosage of the compound of the invention may be in the range from 0.01 micrograms per kilogram body weight (µg/kg) to 100 milligrams per kilogram body weight (mg/kg).

Compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition. In some embodiments, the pharmaceutical composition comprises 0.5% w of active ingredient. In some embodiments, the pharmaceutical composition comprises 20% w of active ingredient.

The present invention also provides a pharmaceutical composition comprising a compound of formula (I) or a pharmaceutically acceptable salt thereof as defined herein, in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as defined herein with a pharmaceutically acceptable adjuvant, diluent or carrier.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the above-mentioned excipients for tablets. Also liquid or semi-solid formulations of the compound of the invention may be filled into hard gelatine capsules.

Compounds of the invention may also be administered in conjunction with other compounds used for the treatment of the above conditions.

The following Examples illustrate the present invention. In the Examples certain techniques were used and these are now described.

High pressure liquid chromatography (HPLC) was performed on a reversed phase (RP) column. A linear gradient was applied using for example mobile phase A (0.1% Formic Acid in MilliQ H2O or 0.1% NH3 in MilliQ H2O or 10 mM NH4OAc and 5% CH3CN in MilliQ H2O, or 0.05% trifluoric acid in MilliQ H2O, or NH4HCO3 in MilliQ H2O (10 mM)) and B (CH3OH or CH3CN). Mass spectrometer (MS) analyses were performed in positive and/or negative ion mode using electrospray ionization (ESI+/−), atmospheric pressure photo ionization (APPI+/−) and/or atmospheric pressure chemical ionization (APCI+/−).

Gas chromatography (GC) was performed on a GC equipped with a mass spectrometer (MS) or a flame ionization detector (FID). The MS ion source was either electron impact (EI), or a chemical ionization (CI, reactant gas: methane). For separation a capillary column was used, for example DB-5MS (J&W Scientific). A linear temperature gradient was applied.

Supercritical Fluid Chromatography (SFC) was performed on a straight phase column. An isocratic flow was applied using mobile phase A (CO2) and for example mobile phase B (MeOH, EtOH or IPA).

Alternatively, high pressure liquid chromatography (HPLC) was performed on a straight phase column. A linear gradient or isocratic flow was applied using for example mobile phase A (heptane) and B (EtOH or IPA).

NMR spectra were recorded on a 300 MHz (or higher field) NMR spectrometer fitted with a probe of suitable configuration. Spectra were recorded at ambient temperature unless otherwise stated. Chemical shifts are given in ppm down- and upfield from TMS (0.00 ppm). The following reference signals were used: TMS δ 0.00, or the residual solvent signal of DMSO-d6 δ 2.49, CD3OD δ 3.30, acetone-d6 2.04, CDCl3 δ 7.25, or D2O δ 4.79 (unless otherwise indicated). Resonance multiplicities are denoted s, d, t, q, m, br and app for singlet, doublet, triplet, quartet, multiplet, broad and apparent, respectively.

List of Abbreviations

DBU 1,8-Diazabicyclo[5.4.0]undec-7-ene
DCM Dichloromethane
DEA Diethyl amine
DIPEA Diisopropyl ethyl amine
DMF Dimethylformamide
DMSO Dimethylsulfoxide
EtOAc Ethyl acetate
HATU 2-(1H-7-Azabenzotriazol-1-yl)-1,1,3,3-tetramethyl uronium hexafluorophosphate methanaminium
IPA iso-propanol
MTBE Methyl tert-butyl ether
rt room temperature, or ambient temperature, approx 20-25° C.
sat saturated
T3P Propane phosphonic anhydride Example 1

(S)-(1-Phenyl-2-(pyridin-2-yl)ethylcarbamoyloxy) methyl isobutyrate

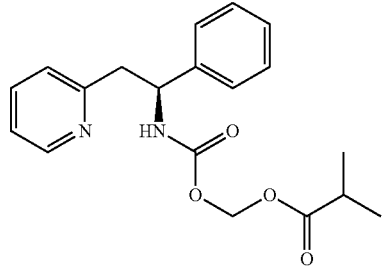 [SMILES: CC(C)C(=O)OCOC(=O)N[C@@H](Cc1ccccn1)c1ccccc1]

Step A

Chloromethyl isobutyrate

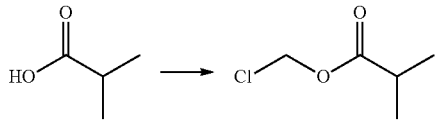

To isobutyric acid (0.600 mL, 6.47 mmol) in DCM (6 mL) was added sodium bicarbonate (2092 mg, 24.91 mmol), tetrabutyl ammonium hydrogen sulfate (220 mg, 0.65 mmol) and water (6 mL). With rapid stirring, chloromethyl sulfochloridate (0.767 mL, 7.44 mmol) was added at rt and the reaction mixture was then stirred at rt overnight. The reaction mixture was then diluted with DCM (10 mL), washed with water (2×10 mL), dried over Na2SO4, filtered and concentrated to give chloromethyl isobutyrate (746 mg, 84%), which was used in the next step without further purification.

1H NMR (500 MHz, CDCl$_3$) δ ppm 1.17 (m, 6H), 2.62 (m, 1H), 5.72 (s, 2H).

Step B (S)-(1-phenyl-2-(pyridin-2-yl)ethylcarbamoyloxy) methyl isobutyrate

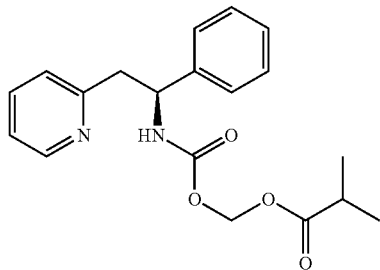 [SMILES: CC(C)C(=O)OCOC(=O)N[C@@H](Cc1ccccn1)c1ccccc1]

Cesium carbonate (1543 mg, 4.74 mmol) and tetrabutylammonium iodide (1749 mg, 4.74 mmol) were added to (S)-1-phenyl-2-(pyridin-2-yl)ethanamine (313 mg, 1.58 mmol) in anhydrous DMF (8 mL) at rt. Carbon dioxide gas was bubbled into the reaction mixture for 30 min, followed by addition of chloromethyl isobutyrate (647 mg, 4.74 mmol) in DMF (2 mL). The reaction mixture was stirred at rt with continued CO$_2$ gas bubbling overnight and continued to stir over the weekend without further CO$_2$ gas addition. The reaction mixture was diluted with water and extracted with EtOAc (3×), the combined organic layers were washed with water (2×), brine, dried over Na$_2$SO$_4$, and concentrated. Purification was done by column chromatography using a gradient of EtOAc in heptane (0-60%) to give the title compound (239 mg, 44.2%).

$^1$H NMR (500 MHz, DMSO-d6) δ ppm 1.00 (m, 6H), 2.46 (m, 1H, partially hidden in DMSO-d6), 3.09 (m, 2H), 5.04 (m, 1H), 5.52 (m, 2H), 7.17-7.24 (m, 3H), 7.27-7.34 (m, 4H), 7.65 (td, 1H), 8.24 (d, 1H), 8.49 (m, 1H).

Example 2

2-Methyl-1-((S)-1-phenyl-2-(pyridin-2-yl)ethylcarbamoyloxy)propyl isobutyrate

There are two different diastereomers of Example 2 due to the two possible configurations at the carbon atom identified with *. These are referred to as Example 2 diastereomer 1 and Example 2 diastereomer 2. Their absolute configurations have not been determined.

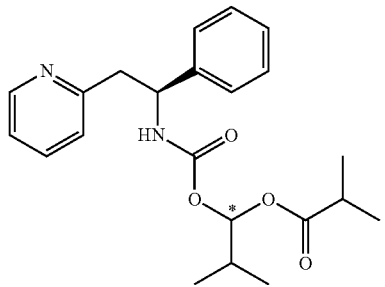 [SMILES: CC(C)C(=O)OC(OC(=O)N[C@@H](Cc1ccccn1)c1ccccc1)C(C)C]

Step A 2-methyl-1-((4-(methylsulfonyl)phenoxy)carbonyloxy)propyl isobutyrate

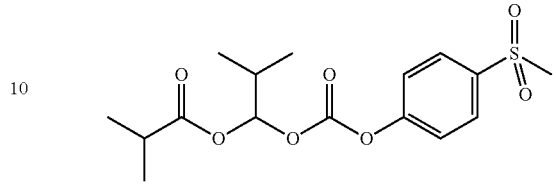

(i) 4-(Methylmercapto)phenol (8.46 g, 57.30 mmol) was taken up in DCM (60 mL) and then the reaction flask was chilled to 0° C., followed by addition of 1-chloro-2-methylpropyl carbonochloridate (4.27 mL, 28.65 mmol). A solution of 4-methylmorpholine (7.87 mL, 71.63 mmol) in DCM (40 mL) was added drop-wise, over 50 min at 0° C. and the resulting mixture stirred at this temperature for 5 minutes, and finally stirred at rt for 150 minutes. The reaction mixture was washed with water (2×), dried over Na$_2$SO$_4$, filtered and evaporated to give 1-chloro-2-methylpropyl 4-(methylthio) phenyl carbonate (13.84 g), which was used in the next step without further purification.

(ii) A mixture of 1-chloro-2-methylpropyl 4-(methylthio) phenyl carbonate (3.50 g, 12.74 mmol), silver(I) oxide (2.95 g, 12.74 mmol) and isobutyric acid (13.00 mL, 140.12 mmol) under an atmosphere of argon was heated to 95° C. for 2 hours. The reaction mixture was cooled to rt and stirred at rt overnight, then diluted with MTBE, filtered through diatomaceous earth and washed with more MTBE. The combined filtrates were washed with water (4×25 mL), sat. aq. sodium bicarbonate (2×25 mL), dried (Na$_2$SO$_4$), and evaporated to give 3.56 g of 2-methyl-1-((4-(methylthio) phenoxy)carbonyloxy)propyl isobutyrate, which was used in the next step without further purification.

(iii) 2-Methyl-1-((4-(methylthio)phenoxy)carbonyloxy) propyl isobutyrate (3.56 g, 10.91 mmol) was taken up in a mixture of acetone (30 mL) and water (7.50 mL), followed by addition of oxone (13.41 g, 21.81 mmol) in portions over 5 min, then stirred at rt for 2 hours. The reaction mixture was filtered and the filtrate washed with MTBE (2×50 mL), the volume was reduced to 50 mL (distilling off the acetone) and then the resulting mixture was separated between MTBE and water. The aqueous layer was extracted with MTBE and the combined organics were dried over Na$_2$SO$_4$, filtered and evaporated to give 1.89 g of the title compound, which was used in the next step without further purification.

Step B:

2-Methyl-1-((S)-1-phenyl-2-(pyridin-2-yl)ethylcarbamoyloxy)propyl isobutyrate

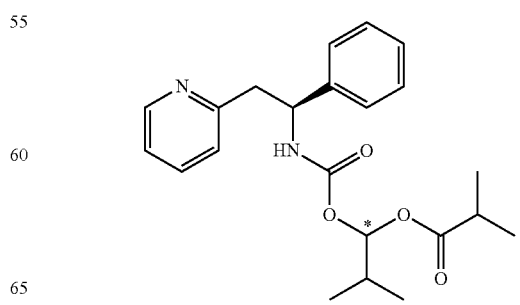

To a stirred mixture of (S)-1-phenyl-2-(pyridin-2-yl)ethanamine (0.215 g, 1.08 mmol) and sodium bicarbonate (0.182 g, 2.17 mmol) in acetonitrile (3 mL) was added 2-methyl-1-((4-(methyl sulfonyl)phenoxy)carbonyloxy)propyl isobutyrate (0.389 g, 1.08 mmol) in acetonitrile (2 mL) and the reaction was stirred at rt for 2 hours. Separated between EtOAc and sat aq NaHCO$_3$, the organic layer was washed with sat aq NaHCO$_3$, dried (Na$_2$SO$_4$) and evaporated to give 413 mg of material, which was purified by column chromatography using a gradient of EtOAc in heptane (0-50%) to give 235 mg as a mixture of the two diastereomers of 2-methyl-1-(S)-1-phenyl-2-(pyridin-2-yl)ethylcarbamoyloxy)propyl isobutyrate.

Analysis and separation of the diasteremers was done on Chiralpak AD-H, 4.6*250 mm; 5 μm, using 10% MeOH/90% CO$_2$ at 3 mL/min flow and Chiralpak AD-H, 20*250 mm; 5 μm, using 10% MeOH/90% CO$_2$ at 50 mL/min flow, respectively.

Example 2, Diastereomer 1

105 mg of diastereomer 1 was obtained by chiral separation as the first eluting diastereomer in 99% optical purity. Mixture of rotamers:
$^1$H NMR (500 MHz, DMSO-d6) δ ppm 0.66-1.07 (m), 1.86 (m), 2.39 (m), 2.98-3.21 (m), 5.01 (m), 6.31 (m), 7.10-7.26 (m), 7.26-7.37 (m), 7.56-7.73 (m), 8.10 (d), 8.43-8.55 (m). Total no of protons in spectrum: 28. Ratio rotamers major/minor: 1/0.15.
MS (ES+APCI+) m/z 385 (M+H)$^+$ Example 2, Diastereomer 2

104 mg of diastereomer 2 were obtained as the second-eluting diastereomer. Mixture of rotamers:
$^1$H NMR (500 MHz, DMSO-d6) δ ppm 0.48-0.69 (m), 0.75-0.87 (m), 0.87-1.07 (m), 1.73 (m), 1.85 (m), 2.40 (m), 2.98 (m), 3.03-3.18 (m), 4.97 (m), 6.22-6.38 (m), 7.13-7.26 (m), 7.26-7.37 (m), 7.65 (m), 7.78 (d), 8.06 (d), 8.48 (m). Total no of protons in spectrum: 28. Ratio rotamers major/minor: 1/0.17.
MS (ES+APCI+) m/z 385 (M+H)$^+$.
Optical purity=99%

Example 3

1-((S)-1-phenyl-2-(pyridin-2-yl)ethylcarbamoyloxy)ethyl acetate

There are two different diastereomers of Example 3 due to the two possible configurations at the carbon atom identified with *. These are referred to as Example 3 diastereomer 1 and Example 3 diastereomer 2. Their absolute configurations have not been determined.

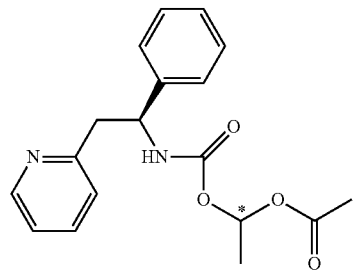 [SMILES: CC(=O)OC(C)OC(=O)N[C@@H](Cc1ccccn1)c1ccccc1]

Step A:

1-((4-(methylsulfonyl)phenoxy)carbonyloxy)ethyl acetate

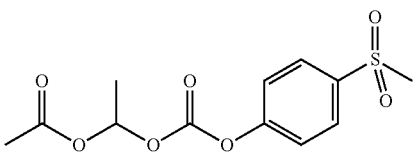 [SMILES: CC(=O)OC(C)OC(=O)Oc1ccc(S(C)(=O)=O)cc1]

(i) A mixture of 1-chloroethyl 4-(methylthio)phenyl carbonate (4.6 g, 18.65 mmol), Silver(I) oxide (4.32 g, 18.65 mmol) and acetic acid (11.75 mL, 205.1 mmol) under an atmosphere of argon was heated to 95° C. for 2 h. The reaction mixture was cooled to rt and diluted with MTBE, filtered through diatomaceous earth, and washed with more MTBE. The combined filtrates were washed with water (4×25 mL), sat. aq. sodium bicarbonate (2×25 mL), dried (Na$_2$SO$_4$), and evaporated to give 1.79 g of 1-((4-(methylthio)phenoxy)carbonyloxy)ethyl acetate which was used in the next step without further purification.

(ii) 1-((4-(Methylthio)phenoxy)carbonyloxy)ethyl acetate (1.79 g, 6.62 mmol) was taken up in a mixture of acetone (16 mL) and water (4.00 mL). Oxone (8.14 g, 13.24 mmol) was added in portions over 5 min, then stirred at rt overnight. The reaction mixture was filtered and the filtrate washed with MTBE (2×50 mL), the volume was reduced to about 50 mL (distilling off the acetone). The product was separated between MTBE and water. The aqueous layer was extracted with MTBE and the combined organics were dried (Na$_2$SO$_4$), filtered and evaporated to give 832 mg of the title compound and used in the next step without further purification.

Step B:

1-((S)-1-phenyl-2-(pyridin-2-yl)ethyl carbamoyloxy)ethyl acetate

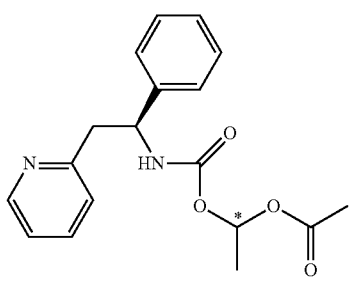 [SMILES: CC(=O)OC(C)OC(=O)N[C@@H](Cc1ccccn1)c1ccccc1]

To a stirred mixture of (S)-1-phenyl-2-(pyridin-2-yl)ethanamine (198 mg, 1 mmol) and sodium bicarbonate (168 mg, 2.00 mmol) in acetonitrile (4 mL) was added 1-((4-(methylsulfonyl)phenoxy)carbonyloxy)ethyl acetate (302 mg, 1.00 mmol) in acetonitrile (1 mL) and the reaction was stirred at rt for 4 hours. The reaction mixture was then separated between EtOAc and sat aq NaHCO$_3$, the organic layer washed with sat aq NaHCO$_3$, brine, dried over Na$_2$SO$_4$ and evaporated. This mixture was pre-purified by column chromatography using a gradient of EtOAc in heptane (0-50%) to give 160 mg of the title compound as mixture of its two diastereomers.

Analysis and separation of the diastereomers was done on Phenomenex LuxC4, 4.6*250 mm; 5 µm, using 30% MeOH+DEA/70% $CO_2$ at 3 mL/min flow and Phenomenex LuxC4, 20*250 mm; 5 µm, using 25% MeOH+DEA/75% $CO_2$ at 50 mL/min flow, respectively.

Example 3, Diastereomer 1

29 mg of diastereomer 1 was obtained by chiral separation as the first eluting diastereomer in 99% optical purity.

$^1$H NMR (500 MHz, DMSO-d6) δ ppm 1.31 (d, 3H), 1.92 (s, 3H), 3.00-3.16 (m, 2H), 5.00 (td, 1H), 6.52 (q, 1H), 7.14-7.25 (m, 3H), 7.30 (d, 4H), 7.65 (t, 1H), 8.13 (d, 1H), 8.50 (d, 1H). The signals in the spectrum were broadened and the splitting of the DMSO-signal could not be seen.

$^{13}$C NMR (126 MHz, DMSO-d6) δ 19.6, 20.7, 44.6, 54.9, 88.7, 121.6, 123.8, 126.4, 126.9, 128.3, 136.2, 143.0, 149.0, 153.2, 158.0, 168.6 ppm. MS (ES+) m/z 328 (M+H)+.

Example 3, Diastereomer 2

39 mg of diastereomer 2 were obtained as the second eluting diastereomer.

$^1$H NMR (500 MHz, DMSO-d6) δ ppm 1.32 (d, 3H), 1.95 (s, 3H), 3.01-3.18 (m, 2H), 5.00 (td, 1H), 6.53 (q, 1H), 7.13-7.24 (m, 3H), 7.29 (d, 4H), 7.65 (t, 1H), 8.17 (d, 1H), 8.49 (d, 1H). The signals in the spectrum were broadened and the splitting of the DMSO-signal could not be seen.

$^{13}$C NMR (126 MHz, DMSO-d6) δ 19.6, 20.7, 44.4, 54.9, 88.6, 121.6, 123.7, 126.4, 126.9, 128.3, 136.2, 143.0, 149.0, 153.1, 158.0, 168.5. MS (ES+) m/z 329 (M+H)$^+$.

Optical purity 98%.

Example 4

1-((S)-1-Phenyl-2-(pyridin-2-yl)ethylcarbamoyloxy) ethyl isobutyrate

There are two different diastereomers of Example 4 due to the two possible configurations at the carbon atom identified with *. These are referred to as Example 4 diastereomer 1 and Example 4 diastereomer 2. Their absolute configurations have not been determined.

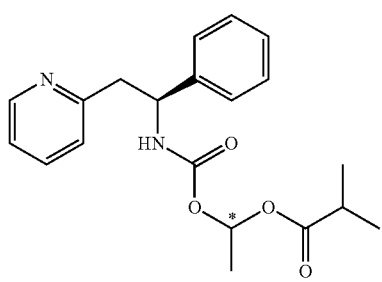 [SMILES: CC(OC(=O)N[C@@H](Cc1ccccn1)c1ccccc1)OC(=O)C(C)C]

Step A:

1-((4-(methylsulfonyl)phenoxy)carbonyloxy)ethyl isobutyrate

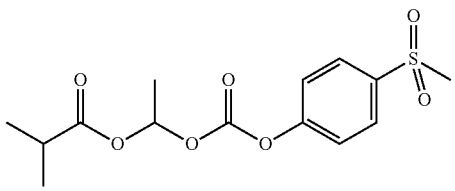 [SMILES: CC(OC(=O)Oc1ccc(S(C)(=O)=O)cc1)OC(=O)C(C)C]

(i) 4-(Methylmercapto)phenol (4.91 g, 35.00 mmol) was taken up in DCM (100 mL) and chilled to 0° C. 1-Chloroethyl chloroformate (1.888 mL, 17.50 mmol) was added. A solution of 4-methylmorpholine (4.81 mL, 43.74 mmol) in DCM (20 mL) was added drop-wise over 10 min at 0° C. and the resulting mixture stirred at this temperature for 5 minutes. The reaction mixture was stirred at rt for 180 min, then diluted with DCM, washed with water (2×), dried over $Na_2SO_4$, filtered and evaporated to give 1-chloroethyl 4-(methylthio)phenyl carbonate (6.94 g), which was used in the next step without further purification.

(ii) A mixture of 1-chloroethyl 4-(methylthio)phenyl carbonate (2.3 g, 9.32 mmol), silver(I) oxide (2.160 g, 9.32 mmol) and isobutyric acid (9.51 ml, 102.55 mmol) under an atmosphere of argon was heated to 95° C. for 2 h. The reaction mixture was cooled to rt and diluted with MTBE, filtered through diatomaceous earth, washed with more MTBE. The combined filtrates were washed with water (4×25 mL), sat. aq. sodium bicarbonate (2×25 mL), dried ($Na_2SO_4$), and evaporated to give 1.16 g of product, which was used in the next step without further purification.

(iii) 1-((4-(Methylthio)phenoxy)carbonyloxy)ethyl isobutyrate (1.16 g, 3.89 mmol) was taken up in a mixture of acetone (12 mL) and water (3.00 mL). Oxone (4.78 g, 7.78 mmol) was added in portions over 5 min, then stirred at rt overnight. The reaction mixture was filtered and the filtrate washed with MTBE (2×50 mL), the volume was reduced to approximately 50 mL by distilling off the acetone, then separated between MTBE and water. The aqueous layer was extracted with MTBE and the combined organics were dried over $Na_2SO_4$, filtered and evaporated to give 531 mg of the title compound, which was used in the next step without further purification.

Step B 1-((S)-1-Phenyl-2-(pyridin-2-yl)ethylcarbamoyloxy) ethyl isobutyrate

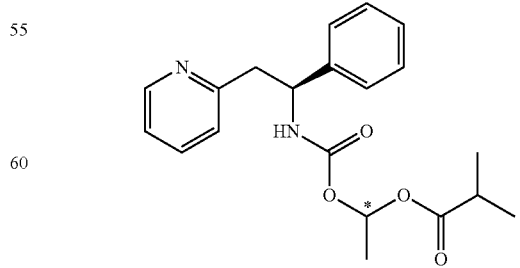

To a stirred mixture of (S)-1-phenyl-2-(pyridin-2-yl) ethanamine (0.300 g, 1.51 mmol) and sodium bicarbonate (0.254 g, 3.03 mmol) in acetonitrile (6 mL) was added 1-((4-(methylsulfonyl)phenoxy)carbonyloxy)ethyl isobutyrate (0.500 g, 1.51 mmol) in acetonitrile (2 mL) and the reaction was stirred overnight. The mixture was separated between EtOAc and sat aq NaHCO₃, the organic layer was washed with sat aq NaHCO₃, brine, dried over Na₂SO₄ and evaporated to give 0.70 g., which was purified by column chromatography using a gradient of EtOAc in heptane (0-50%) to give the title compound (0.309 g, 57.2%) as mixture of the two diastereomers.

Analysis and separation of the diastereomers was done on Phenomenex LuxC4, 4.6*250 mm; 5 μm, using 15% MeOH+DEA/85% CO₂ at 3 mL/min flow and Phenomenex LuxC4, 20*250 mm; 5 μm, using 15% MeOH+DEA/85% CO₂ at 50 mL/min flow, respectively.

Example 4, Diastereomer 1

25 mg of diastereomer 1 was obtained by chiral separation as the first eluting diastereomer in 99% optical purity. Mixture of rotamers:

¹H NMR (500 MHz, DMSO-d6) δ ppm 0.86-1.05 (m), 1.19 (d), 1.32 (d), 2.31-2.44 (m), 2.98-3.20 (m), 4.94-5.07 (m), 6.48 (d), 6.52 (q), 7.15-7.25 (m), 7.25-7.34 (m), 7.60-7.70 (m), 7.77 (d), 8.06-8.18 (m), 8.44-8.55 (m). Total no of protons in spectrum: 24. Ratio major/minor: 1:0.07.

MS (ES+APCI+) m/z 357 (M+H)⁺.

UV Purity=100%.

Example 4, Diastereomer 2

25 mg of diastereomer 2 were obtained as second eluting isomer. Mixture of rotamers:

¹H NMR (500 MHz, DMSO-d6) δ ppm 0.82-0.94 (m), 0.94-1.04 (m), 1.25 (d), 1.32 (d), 2.24-2.32 (m), 2.34-2.44 (m), 3.00-3.17 (m), 5.02 (td), 6.48 (d), 6.52 (q), 7.15-7.25 (m), 7.25-7.38 (m), 7.55-7.77 (m), 8.16 (d), 8.44-8.57 (m). Total no of protons in spectrum: 24. Ratio major/minor: 1:0.08.

MS (ES+APCI+) m/z 357 (M+H)⁺.

UV Purity=100%.

Optical purity=99%.

Examples 5 to 12 use a common intermediate, the preparation of which is now described.

Preparation of Common Intermediate for Examples 5 to 12

2-((S)-2-phenyl-2-((S)-pyrrolidin-2-iumcarboxamido) ethyl)pyridinium dichloride (which can also be named as: (S)—N—((S)-1-phenyl-2-(pyridin-2-yl)ethyl)pyrrolidine-2-carboxamide dihydrochloride)

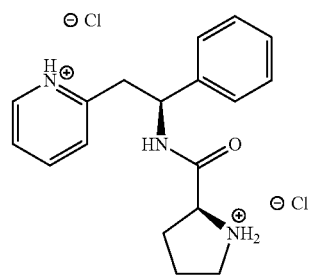

Step A (S)-tert-butyl 2-((S)-1-phenyl-2-(pyridin-2-yl)ethylcarbamoyl)pyrrolidine-1-carboxylate

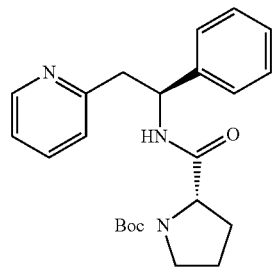 [SMILES: O=C(N[C@@H](Cc1ccccn1)c1ccccc1)[C@@H]1CCCN1 ; "Boc"]

T3P (50% wt. in DMF, 0.86 mL, 1.47 mmol) was added dropwise to a solution of (1S)-1-phenyl-2-(pyridin-2-yl) ethan-1-amine (200 mg, 0.737 mmol), Boc-L-proline (159 mg, 0.737 mmol) and DIPEA (0.64 mL, 3.69 mmol) in CH₂Cl₂ (7.4 mL) at 0° C. The reaction was gradually warmed to rt while stirring overnight. The organic layer was washed twice with 5% aq. NaHCO₃, once with brine, dried over Na₂SO₄, filtered and concentrated. The product was purified using a 50 g snap column, eluting with a gradient of MeOH and CH₂Cl₂ (0% MeOH/100% CH₂Cl₂→10% MeOH/90% CH₂Cl₂), yielding the title compound 305 mg (>100%).

¹H NMR (300 MHz, CDCl₃): ppm 1.35 (s, 9H), 1.70-1.90 (m, 2H), 2.05-2.19 (m, 2H), 3.13 (dd, 1H), 3.29-3.39 (m, 1H), 3.46-3.62 (m, 2H), 4.20-4.29 (m, 2H), 5.39 (q, 1H), 6.91 (d, 1H), 7.09-7.14 (m, 1H), 7.16-7.23 (m, 5H), 7.49 (td, 1H), 8.45-8.59 (m, 1H).

Alternative Method:

Boc-L-Pro-OH (2.0 g, 9.29 mmol) was dissolved in anhydrous DMF (15 mL). HATU (3.7 g, 9.76 mmol) and Hunig's base (5.3 mL, 30.66 mmol) were added and the mixture was stirred at rt for 30 minutes. Then, 2-[(2S)-2-azaniumyl-2-phenylethyl]pyridin-1-ium dichloride (2.5 g, 9.29 mmol) was added to the solution and the mixture was stirred for 3 hours 30 minutes at rt. Water was added and the mixture was extracted 3× with EtOAc. The organic phase was washed with brine, dried over Na₂SO₄, filtered and concentrated under reduced pressure. The product was purified on a SiO₂ column, eluting with a gradient (0% MeOH/ 50% EtOAc/50% heptane→0% MeOH/100% EtOAc/0% heptane→10% MeOH/90% EtOAc/0% heptane) and then on a C-18 column, eluting with a gradient of MeOH and water (0 to 100% MeOH), yielding 2.9 g (78%) of the title compound.

¹H NMR (300 MHz, CDCl₃): ppm 1.35 (s, 9H), 1.70-1.90 (m, 2H), 2.05-2.19 (m, 2H), 3.13 (dd, J=13.8, 7.1 Hz, 1H), 3.29-3.39 (m, 1H), 3.46-3.62 (m, 2H), 4.20-4.29 (m, 1H), 5.39 (q, J=6.8 Hz, 1H), 6.91 (d, J=7.3 Hz, 1H), 7.09-7.14 (m, 1H), 7.16-7.23 (m, 5H), 7.49 (td, J=7.63, 1.8 Hz, 1H), 8.45-8.59 (m, 1H).

Step B (S)—N—((S)-1-phenyl-2-(pyridin-2-yl)ethyl)pyrrolidine-2-carboxamide dihydrochloride

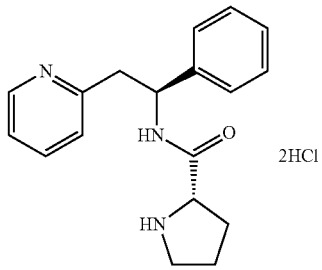 [SMILES: O=C(N[C@@H](Cc1ccccn1)c1ccccc1)[C@@H]1CCCN1]

At 0° C., (S)-tert-butyl 2-((S)-1-phenyl-2-(pyridin-2-yl)ethylcarbamoyl)pyrrolidine-1-carboxylate (305 mg, 0.771 mmol) was dissolved in a 4 M HCl solution in 1,4-dioxane (7.7 mL, 30.8 mmol). The reaction was gradually warmed to rt while stirring overnight. The volatiles were removed under vacuum and the product was triturated in MTBE. The solid was recovered by filtration on a Buchner funnel, washed with MTBE and dried under vacuum affording 263 mg (93%) of the title compound as dihydrochloride salt.

$^1$H NMR (300 MHz, DMSO-$d_6$): ppm 1.61-1.84 (m, 3H), 2.30-2.36 (m, 1H), 3.05-3.11 (m, 2H), 3.39-3.47 (m, 2H), 4.05-4.20 (m, 2H), 5.34 (q, 1H), 7.17-7.41 (m, 5H), 8.20-8.42 (m, 1H), 8.67-8.75 (m, 1H), 9.45-9.62 (m, 2H).

Alternative Method:

tert-Butyl (2S)-2-{[(1S)-1-phenyl-2-(pyridin-2-yl)ethyl]carbamoyl}pyrrolidine-1-carboxylate (2.9 g, 7.33 mmol) was dissolved in a 4 M HCl solution in 1,4-dioxane (73 mL, 293.31 mmol). The reaction mixture was stirred at rt for 3 h. The volatiles were removed under vacuum and the product was triturated in MTBE. The solid was recovered by filtration on a Büchner funnel, washed with MTBE and dried under vacuum affording 2.7 g (100%) of (2S)-2-{[(1S)-1-phenyl-2-(pyridin-1-ium-2-yl)ethyl]carbamoyl}pyrrolidin-1-ium.

$^1$H NMR (300 MHz, D$_2$O): ppm 1.66-1.83 (m, 3H), 2.20-2.26 (m, 1H), 3.14 (t, J=6.9 Hz, 2H), 3.34 (dd, J=14.1, 8.2 Hz, 1H), 3.51 (dd, J=14.4, 7.3 Hz, 1H), 4.18 (dd, J=8.5, 6.2 Hz, 1H), 5.11 (t, J=7.9 Hz, 1H), 7.06-7.10 (m, 2H), 7.15-7.21 (m, 3H), 7.61-7.70 (m, 2H), 8.23 (dt, J=7.9, 1.5 Hz, 1H), 8.37 (d, J=5.8 Hz, 1H).

Example 5

(S)-1-((S)-2-Amino-3-methylbutanoyl)-N—((S)-1-phenyl-2-(pyridin-2-yl)ethyl)pyrrolidine-2-carboxamide

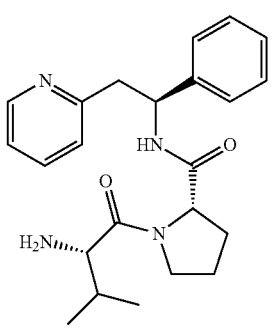 [SMILES: CC(C)[C@H](N)C(=O)N1CCC[C@H]1C(=O)N[C@@H](Cc1ccccn1)c1ccccc1]

The title compound was prepared as the dihydrochloride of (S)-1-((S)-2-amino-3-methylbutanoyl)-N—((S)-1-phenyl-2-(pyridin-2-yl)ethyl)pyrrolidine-2-carboxamide

Step A tert-Butyl (S)-3-methyl-1-oxo-1-((S)-2-((S)-1-phenyl-2-(pyridin-2-yl)ethylcarbamoyl)pyrrolidin-1-yl)butan-2-ylcarbamate

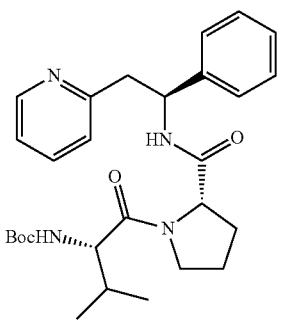 [SMILES: CC(C)[C@H](NC(=O)OC(C)(C)C)C(=O)N1CCC[C@H]1C(=O)N[C@@H](Cc1ccccn1)c1ccccc1]

T3P (50% wt. in DMF, 0.83 mL, 1.42 mmol) was added dropwise to a solution of (S)—N—((S)-1-phenyl-2-(pyridin-2-yl)ethyl)pyrrolidine-2-carboxamide dihydrochloride salt (263 mg, 0.714 mmol), Boc-L-Valine (155 mg, 0.714 mmol) and DIPEA (0.62 mL, 3.57 mmol) in DCM (7 mL) at 0° C. The reaction was gradually warmed to rt under stirring overnight. The organic layer was washed twice with 5% aq. NaHCO$_3$, once with brine, dried over Na$_2$SO$_4$, filtered and concentrated. The product was purified using a 50 g snap column, eluting with a gradient of MeOH and CH$_2$Cl$_2$ (5% MeOH/95% CH$_2$Cl$_2$→10% MeOH/90% CH$_2$Cl$_2$), yielding the title compound 258 mg (73%).

$^1$H NMR (300 MHz, CDCl$_3$): ppm 0.91 (d, 3H), 1.00 (d, 3H), 1.43 (s, 9H), 1.85-1.99 (m, 2H), 2.00-2.16 (m, 1H), 2.17-2.21 (m, 1H), 3.12-3.27 (m, 2H), 3.47-3.62 (m, 2H), 3.63-3.78 (m, 1H), 4.32 (dd, 1H), 4.58 (d, 1H), 5.23-5.35 (m, 2H), 6.97 (d, 1H), 7.10 (dd, 1H), 7.14-7.30 (m, 5H), 7.50 (td, 1H), 7.84 (d, 1H), 8.48 (dd, 1H).

Step B (S)-1-((S)-2-Amino-3-methylbutanoyl)-N—((S)-1-phenyl-2-(pyridin-2-yl)ethyl)pyrrolidine-2-carboxamide dihydrochloride

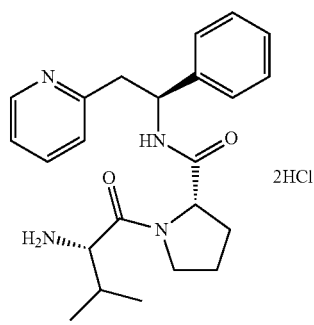 [SMILES: CC(C)[C@H](N)C(=O)N1CCC[C@H]1C(=O)N[C@@H](Cc1ccccn1)c1ccccc1]

tert-Butyl (S)-3-methyl-1-oxo-1-((S)-2-((S)-1-phenyl-2-(pyridin-2-yl)ethylcarbamoyl)pyrrolidin-1-yl)butan-2-ylcarbamate (258 mg, 0.522 mmol) was dissolved in a 4 M HCl solution in 1,4-dioxane (5.2 mL, 30.8 mmol). The reaction mixture was stirred overnight. The volatiles were removed under vacuum and the product was triturated in EtOAc. The solid was recovered by filtration on a Buchner funnel, then triturated in Et$_2$O. After filtration on a Buchner funnel, the solid was dried under vacuum affording 200 mg (82%) of the title compound as dihydrochloride salt. The title compound as the dihydrochloride salt was then converted to the free base by techniques known to one of ordinary skill in the art. Alternatively, the title compound may be prepared as a fumarate salt by methods known to one of ordinary skill in the art.

$^1$H NMR (300 MHz, CD$_3$OD): ppm 0.97 (d, 3H), 1.04 (d, 3H), 1.68-1.79 (m, 1H), 1.86-2.05 (m, 2H), 2.13-2.27 (m, 2H), 3.50-3.61 (m, 3H), 3.68-3.75 (m, 1H), 4.02 (d, 1H), 4.45 (dd, 1H), 5.40 (dd, 1H), 7.31-7.43 (m, 5H), 7.90 (t, 1H), 8.02 (d, 1H), 8.51 (td, 1H), 8.75 (d, 1H).

[M+H]+=395.27

Example 6

(S)-1-((S)-2,6-Diaminohexanoyl)-N—((S)-1-phenyl-2-(pyridin-2-yl)ethyl)pyrrolidine-2-carboxamide

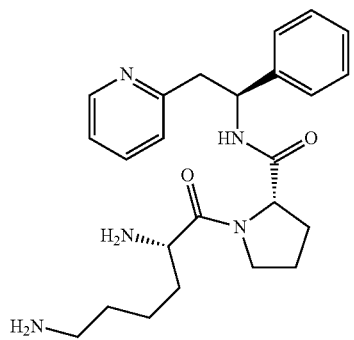 [SMILES: NCCCC[C@H](N)C(=O)N1CCC[C@H]1C(=O)N[C@@H](Cc1ccccn1)c1ccccc1]

The title compound was prepared as the trichloride, 2-[(2S)-2-{[(2S)-1-[(2S)-2,5-diazaniumylhexanoyl]pyrrolidin-2-yl]formamido}-2-phenylethyl]pyridin-1-ium trichloride Step A tert-Butyl (S)-6-oxo-6-((S)-2-((S)-1-phenyl-2-(pyridin-2-yl)ethylcarbamoyl)pyrrolidin-1-yl)hexane-1,5-diyldicarbamate

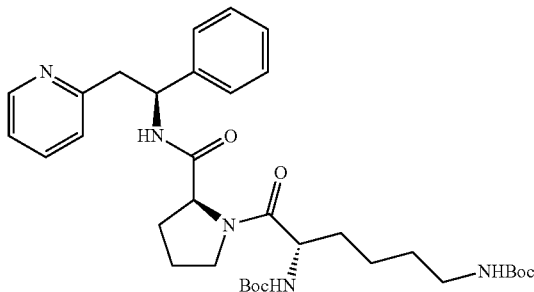 [SMILES: CC(C)(C)OC(=O)NCCCC[C@H](NC(=O)OC(C)(C)C)C(=O)N1CCC[C@H]1C(=O)N[C@@H](Cc1ccccn1)c1ccccc1]

N-alpha, N-epsilon-bis(tert-Butoxycarbonyl)-L-lysine dicyclohexylammonium salt (287 mg, 0.54 mmol) was dissolved in anhydrous DMF (4 mL). HATU (217 mg, 0.57 mmol) and DIPEA (0.21 mL, 1.19 mmol) were added and the mixture was stirred at rt for 30 minutes. Then, (2S)-2-{[(1S)-1-phenyl-2-(pyridin-1-ium-2-yl)ethyl]carbamoyl}pyrrolidin-1-ium dichloride (200 mg, 0.54 mmol) was added to the solution and the mixture was stirred for 18 h at rt. Water was added and the mixture was extracted 3× with EtOAc. The organic phase was washed with brine, dried over Na$_2$SO$_4$, filtered and concentrated under reduced pressure. The product was purified on a SiO$_2$ column, eluting with a gradient (0% MeOH/50% EtOAc/50% heptane→0% MeOH/100% EtOAc/0% heptane→10% MeOH/90% EtOAc/0% heptane) then on a C-18 column, eluting with a gradient of MeOH and water (0 to 100% MeOH), yielding 80 mg (24%) of the title compound.

$^1$H NMR (300 MHz, CDCl$_3$): ppm 1.34-1.39 (m, 2H), 1.41 (s, 9H), 1.43 (s, 9H), 1.52-1.64 (m, 3H), 1.68-2.02 (m, 4H), 2.08-2.22 (m, 2H), 3.02-3.16 (m, 3H), 3.20-3.28 (m, 1H), 3.48-3.57 (m, 1H), 3.60-3.70 (m, 1H), 4.40-4.51 (m, 1H), 4.54-4.57 (m, 1H), 4.97-5.08 (m, 1H), 5.29-5.39 (m, 2H), 7.00 (d, 1H), 7.10-7.32 (m, 6H), 7.52 (td, 1H), 7.86 (d, 1H), 8.49 (d, 1H).

Step B

Synthesis of 2-[(2S)-2-{[(2S)-1-[(2S)-2,5-diazaniumylhexanoyl]pyrrolidin-2-yl]formamido}-2-phenylethyl]pyridin-1-ium trichloride

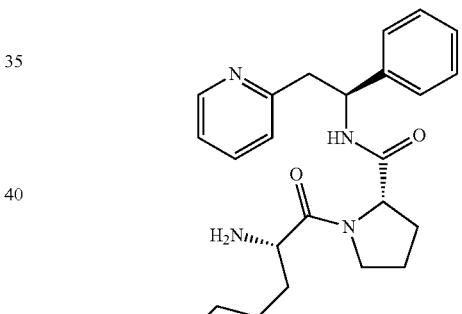

tert-Butyl (S)-6-oxo-6-((S)-2-((S)-1-phenyl-2-(pyridin-2-yl)ethylcarbamoyl)pyrrolidin-1-yl)hexane-1,5-diyldicarbamate (80 mg, 0.13 mmol) was dissolved in a 4 M HCl solution in 1,4-dioxane (1.6 mL, 6.4 mmol). The reaction was stirred at rt for 18 hours. The volatiles were removed under vacuum and the product was triturated in MTBE. The solid was recovered by filtration on a Büchner funnel, washed with MTBE and dried under vacuum. The solid was dissolved in water and freeze dried to afford 60 mg (88%) of the title compound.

$^1$H NMR (300 MHz, D$_2$O): ppm 1.23-1.35 (m, 2H), 1.46-1.59 (m, 3H), 1.65-1.80 (m, 4H), 2.04-2.13 (m, 1H), 2.80 (t, 2H), 3.31-3.43 (m, 2H), 3.47-3.57 (m, 2H), 4.16 (t, 1H), 4.28 (t, 1H), 5.11 (t, 1H), 7.10-7.13 (m, 2H), 7.16-7.26 (m, 3H), 7.68-7.73 (m, 2H), 8.31 (td, 1H), 8.42 (dd, 1H);

[M+H]$^+$=424.2.

Example 7

(S)-1-((S)-2-Amino-3-(1H-imidazol-4-yl)propanoyl)-N—((S)-1-phenyl-2-(pyridin-2-yl)ethyl) pyrrolidine-2-carboxamide

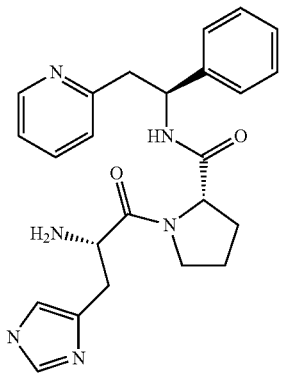 [SMILES: N[C@@H](Cc1c[nH]cn1)C(=O)N1CCC[C@H]1C(=O)N[C@@H](Cc1ccccn1)c1ccccc1]

The title compound was prepared as the trichloride 2-[(2S)-2-{[(2S)-1-[(2S)-2-azaniumyl-3-(1H-imidazol-1-ium-4-yl)propanoyl]pyrrolidin-2-yl]formamido}-2-phenylethyl]pyridin-1-ium trichloride Step A tert-Butyl (S)-3-(1H-imidazol-4-yl)-1-oxo-1-((S)-2-((S)-1-phenyl-2-(pyridin-2-yl)ethylcarbamoyl)pyrrolidin-1-yl)propan-2-ylcarbamate

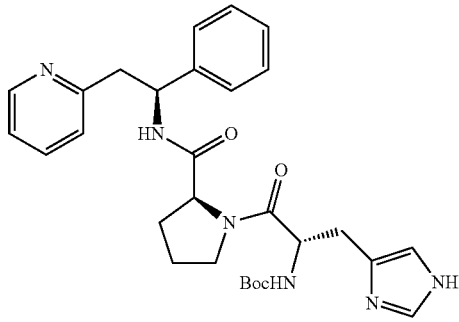 [SMILES: CC(C)(C)OC(=O)N[C@@H](Cc1c[nH]cn1)C(=O)N1CCC[C@H]1C(=O)N[C@@H](Cc1ccccn1)c1ccccc1]

Boc-His-OH (166 mg, 0.65 mmol) was dissolved in anhydrous DMF (4 mL). HATU (260 mg, 0.68 mmol) and DIPEA (0.38 mL, 2.85 mmol) were added and the mixture was stirred at rt for 30 minutes. Then, 2-((S)-2-phenyl-2-((S)-pyrrolidin-2-iumcarboxamido)ethyl)pyridinium chloride (240 mg, 0.65 mmol) was added and the mixture was stirred for 66 hours at rt. Water was added and the mixture was extracted 3× with EtOAc. The organic phase was washed with brine, dried over Na$_2$SO$_4$, filtered and concentrated under reduced pressure. The product was purified on a SiO$_2$ column, eluting with a gradient of MeOH and CH$_2$Cl$_2$ (0% to 13% MeOH) then on a C-18 column, eluting with a gradient of MeOH and water (0 to 100% MeOH), yielding 100 mg (29%) of the title compound.

$^1$H NMR (300 MHz, CDCl$_3$): ppm 1.44 (s, 9H), 1.77-2.00 (m, 3H), 2.05-2.19 (m, 1H), 3.03-3.14 (m, 2H), 3.23 (dd, 1H), 3.40 (dd, 1H), 3.52-3.58 (m, 1H), 4.50-4.62 (m, 2H), 5.43-5.50 (m, 2H), 6.91-6.97 (m, 2H), 7.13-7.27 (m, 5H), 7.53 (t, 1H), 7.65 (s, 1H), 8.53 (d, 1H), 8.67 (d, 1H).

Step B 2-((S)-2-((S)-1-((S)-2-Ammonio-3-(1H-imidazol-1-ium-4-yl)propanoyl)pyrrolidine-2-carboxamido)-2-phenylethyl)pyridinium trichloride

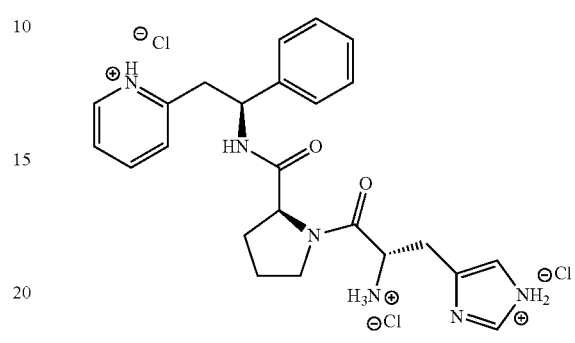

tert-Butyl (S)-3-(1H-imidazol-4-yl)-1-oxo-1-((S)-2-((S)-1-phenyl-2-(pyridin-2-yl)ethylcarbamoyl)pyrrolidin-1-yl)propan-2-ylcarbamate (100 mg, 0.19 mmol) was dissolved in a 4 M HCl solution in 1,4-dioxane (2.3 mL, 9.39 mmol). The reaction mixture was stirred at rt for 18 h. The volatiles were removed under vacuum and the product was triturated in MTBE. The solid was recovered by filtration on a Büchner funnel, washed with MTBE and dried under vacuum. The solid was dissolved in water and freeze dried to afford 85 mg (69%) of the title compound.

$^1$H NMR (300 MHz, D$_2$O): ppm 1.50-1.58 (m, 1H), 1.69-1.76 (m, 2H), 2.07-2.14 (m, 1H), 3.12-3.21 (m, 3H), 3.38 (dd, 7.3 Hz, 1H), 3.48-3.56 (m, 2H), 4.32 (t, 1H), 4.43 (t, 1H), 5.14 (t, 1H), 7.08-7.12 (m, 2H), 7.15-7.23 (m, 3H), 7.26 (s, 1H), 7.65-7.70 (m, 2H), 8.26 (td, 1H), 8.39 (d, 1H), 8.49 (d, 1H);

[M+H]$^+$=433.2;
[M+Na]$^+$=455.1.

Example 8

2-((S)-2-((S)-1-((S)-2-Amino-3-(4-hydroxyphenyl)propanoyl)pyrrolidine-2-carboxamido)-2-phenylethyl)pyridine dihydrochloride

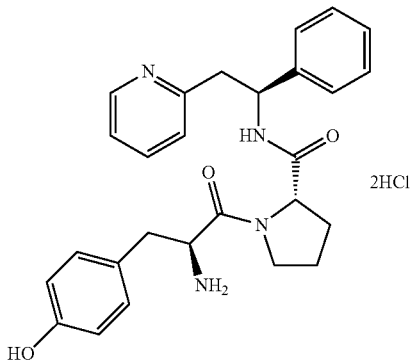 [SMILES: N[C@@H](Cc1ccc(O)cc1)C(=O)N1CCC[C@H]1C(=O)N[C@@H](Cc1ccccn1)c1ccccc1]

The title compound can also be named as: 2-[(2S)-2-{[(2S)-1-[(2S)-2-azaniumyl-3-(4-hydroxyphenyl)propanoyl]pyrrolidin-2-yl]formamido}-2-phenylethyl]pyridin-1-ium dichloride Step A tert-Butyl (S)-3-(4-hydroxyphenyl)-1-oxo-1-((S)-2-((S)-1-phenyl-2-(pyridin-2-yl)ethylcarbamoyl)pyrrolidin-1-yl)propan-2-ylcarbamate

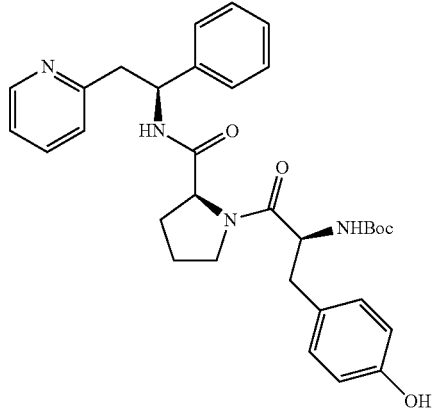 [SMILES: CC(C)(C)OC(=O)N[C@@H](Cc1ccc(O)cc1)C(=O)N1CCC[C@H]1C(=O)N[C@@H](Cc1ccccn1)c1ccccc1]

Boc-Tyr-OH (229 mg, 0.81 mmol) was dissolved in anhydrous DMF (5 mL). HATU (325 mg, 0.86 mmol) and DIPEA (0.47 mL, 2.69 mmol) were added and the mixture was stirred at rt for 30 minutes. Then, 2-((S)-2-phenyl-2-((S)-pyrrolidin-2-iumcarboxamido)ethyl)pyridinium chloride (300 mg, 0.81 mmol) was added to the solution and the mixture was stirred for 66 h at rt. Water was added and the mixture was extracted 3× with EtOAc. The organic phase was washed with brine, dried over Na₂SO₄, filtered and concentrated under reduced pressure. The product was purified on SiO₂ column, eluting with a (0% MeOH/50% EtOAc/50% heptane→0% MeOH/100% EtOAc/0% heptane→15% MeOH/85% EtOAc/0% heptane) then on a C-18 column, eluting with a gradient of MeOH and water (0 to 100% MeOH), yielding 180 mg (40%) of the title compound.

$^1$H NMR (300 MHz, CDCl$_3$): ppm 1.44 (s, 9H), 1.73-2.02 (m, 3H), 2.16-2.22 (m, 1H), 2.92-3.09 (m, 4H), 3.35-3.42 (m, 1H), 3.48-3.51 (m, 1H), 3.53-3.68 (m, 1H), 4.48-4.51 (m, 1H), 4.65-4.73 (m, 1H), 5.06-5.14 (m, 1H), 5.43 (d, 1H), 6.61 (d, 1H), 6.86 (d, 2H), 6.94-6.99 (m, 2H), 7.08-7.26 (m, 6H), 7.42 (dd, 1H), 8.49 (d, 1H), 8.63 (s, 1H).

Step B:

2-((S)-2-((S)-1-((S)-2-Ammonio-3-(4-hydroxyphenyl)propanoyl)pyrrolidine-2-carboxamido)-2-phenylethyl)pyridinium dichloride

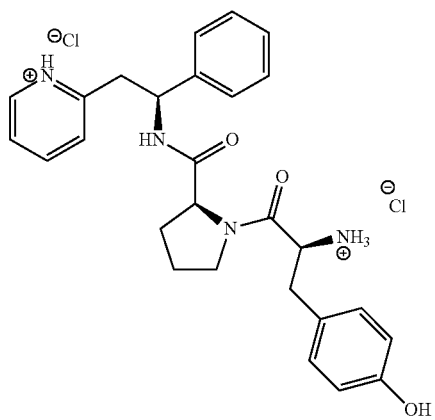

tert-Butyl (S)-3-(4-hydroxyphenyl)-1-oxo-1-((S)-2-((S)-1-phenyl-2-(pyridin-2-yl)ethylcarbamoyl)pyrrolidin-1-yl)propan-2-ylcarbamate (180 mg, 0.32 mmol) was dissolved in a 4 M HCl solution in 1,4-dioxane (3.2 mL, 12.89 mmol). The reaction was stirred at rt for 18 hours. The volatiles were removed under vacuum and the product was triturated in MTBE. The solid was recovered by filtration on a Büchner funnel, washed with MTBE and dried under vacuum. The solid was dissolved in water and freeze dried to afford 150 mg (88%) of the title compound.

$^1$H NMR (300 MHz, D$_2$O): ppm 1.48-1.57 (m, 1H), 1.68-1.73 (m, 2H), 1.98-2.05 (m, 1H), 2.68-2.76 (m, 1H), 2.93-3.00 (m, 1H), 3.10-3.19 (m, 1H), 3.40-3.63 (m, 3H), 4.20-4.28 (m, 2H), 5.14 (t, 1H), 6.65 (d, 2H), 6.96 (d, 2H), 7.13-7.22 (m, 5H), 7.63-7.66 (m, 2H), 8.19-8.22 (m, 1H), 8.40 (d, 1H);

[M+H]$^+$=459.2.

Example 9

2-((S)-2-((S)-1-((S)-2-Amino-3-(1H-indol-3-yl)propanoyl)pyrrolidine-2-carboxamido)-2-phenylethyl)pyridine dihydrochloride

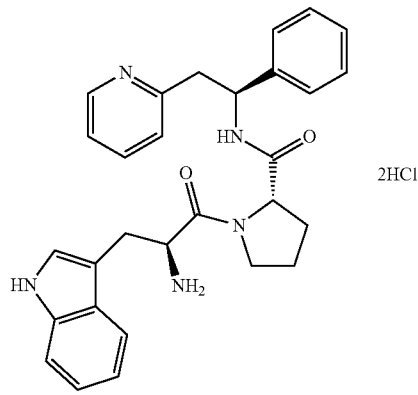 [SMILES: N[C@@H](Cc1c[nH]c2ccccc12)C(=O)N1CCC[C@H]1C(=O)N[C@@H](Cc1ccccn1)c1ccccc1]

The title compound can also be named: 2-[(2S)-2-{[(2S)-1-[(2S)-2-azaniumyl-3-(1H-indol-3-yl)propanoyl]pyrrolidin-2-yl]formamido}-2-phenylethyl]pyridin-1-ium dichloride Step A tert-Butyl (S)-3-(1H-indol-3-yl)-1-oxo-1-((S)-2-((S)-1-phenyl-2-(pyridin-2-yl)ethylcarbamoyl)pyrrolidin-1-yl)propan-2-ylcarbamate

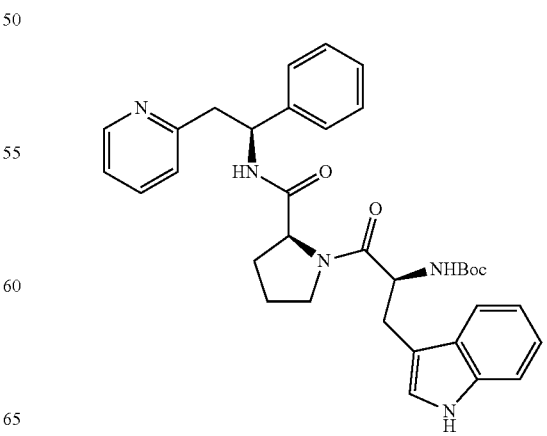

Boc-Trp-OH (207 mg, 0.68 mmol) was dissolved in anhydrous DMF (4 mL). HATU (271 mg, 0.71 mmol) and DIPEA (0.39 mL, 2.24 mmol) were added and the mixture was stirred at rt for 30 minutes. Then, (2S)-2-{[(1S)-1-phenyl-2-(pyridin-1-ium-2-yl)ethyl]carbamoyl}pyrrolidin-1-ium dichloride (250 mg, 0.68 mmol) was added and the mixture was stirred for 18 hours at rt. Water was added and the mixture was extracted 3× with EtOAc. The organic phase was washed with brine, dried over $Na_2SO_4$, filtered and concentrated under reduced pressure. The product was purified on a $SiO_2$ column, eluting with a gradient of (0% MeOH/50% EtOAc/50% heptane→0% MeOH/100% EtOAc/0% heptane→15% MeOH/85% EtOAc/0% heptane), yielding 410 mg (Quantitative) of the title compound.

$^1$H NMR (300 MHz, $CDCl_3$): ppm 1.44 (s, 9H), 1.77-1.89 (m, 3H), 2.14-2.24 (m, 1H), 3.03-3.24 (m, 4H), 3.28-3.36 (m, 2H), 3.54-3.65 (m, 1H), 4.52-4.58 (m, 1H), 4.79-4.88 (m, 1H), 5.12-5.27 (m, 1H), 5.34-5.41 (m, 1H), 6.63 (d, 1H), 6.94-7.31 (m, 8H), 7.38-7.53 (m, 3H), 7.62-7.67 (m, 1H), 8.59 (d, 1H), 9.87 (s, 1H).

Step B 2-((S)-2-((S)-1-((S)-2-Ammonio-3-(1H-indol-3-yl)propanoyl)pyrrolidine-2-carboxamido)-2-phenylethyl)pyridinium dichloride

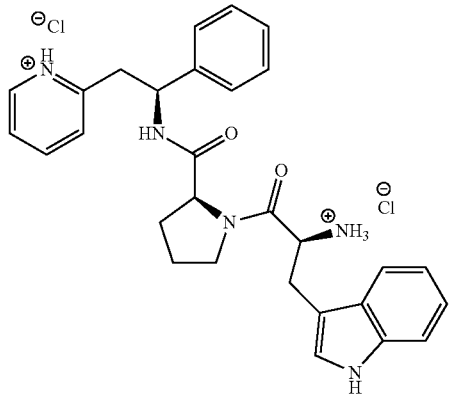

tert-Butyl (S)-3-(1H-indol-3-yl)-1-oxo-1-((S)-2-((S)-1-phenyl-2-(pyridin-2-yl)ethylcarbamoyl)pyrrolidin-1-yl)propan-2-ylcarbamate (395 mg, 0.68 mmol) was dissolved in a 1 M HCl solution in $Et_2O$ (27.0 mL, 27.20 mmol). The reaction mixture was stirred at rt for 4 h. The product was triturated in $Et_2O$ and the solid was recovered by filtration on a Büchner funnel, washed with $Et_2O$ and dried under vacuum. The solid was dissolved in water and freeze dried to afford 175 mg (44%) of the title compound.

$^1$H NMR (300 MHz, $D_2O$): ppm 1.41-1.53 (m, 1H), 1.63-1.72 (m, 2H), 1.93-2.04 (m, 1H), 2.85 (dd, 1H), 2.94-3.55 (m, 5H), 4.19-4.31 (m, 2H), 5.08 (t, 1H), 6.90-7.31 (m, 9H), 7.38 (d, 1H), 7.55-7.58 (m, 2H), 8.15 (t, 1H), 8.31 (d, 1H);

$[M+H]^+$=482.2, $[M+Na]^+$=504.1.

Example 10

(S)-1-((S)-2-Amino-3-phenylpropanoyl)-N—((S)-1-phenyl-2-(pyridin-2-yl)ethyl)pyrrolidine-2-carboxamide

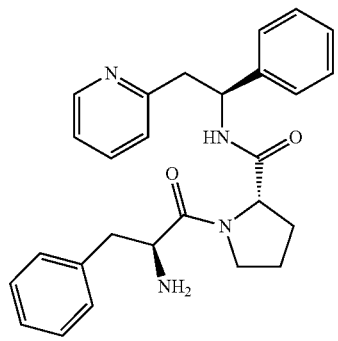 [SMILES: N[C@@H](Cc1ccccc1)C(=O)N1CCC[C@H]1C(=O)N[C@@H](Cc1ccccn1)c1ccccc1]

The title compound was prepared as 2-[(2S)-2-{[(2S)-1-[(2S)-2-azaniumyl-3-phenylpropanoyl]pyrrolidin-2-yl]formamido}-2-phenylethyl]pyridin-1-ium dichloride Step A tert-Butyl (S)-1-oxo-3-phenyl-1-((S)-2-((S)-1-phenyl-2-(pyridin-2-yl)ethylcarbamoyl)pyrrolidin-1-yl)propan-2-ylcarbamate

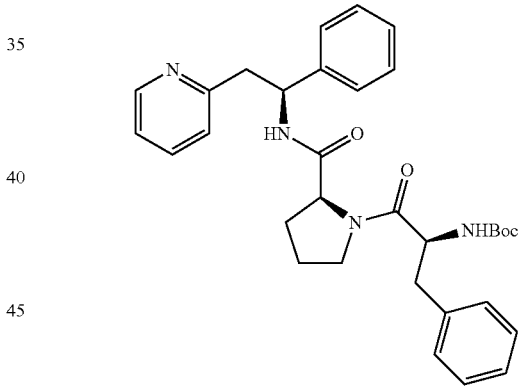

Boc-Phe-OH (180 mg, 0.68 mmol) was dissolved in anhydrous DMF (4 mL). HATU (271 mg, 0.71 mmol) and DIPEA (0.39 mL, 2.24 mmol) were added and the mixture was stirred at rt for 30 minutes. Then, (2S)-2-{[(1S)-1-phenyl-2-(pyridin-1-ium-2-yl)ethyl]carbamoyl}pyrrolidin-1-ium dichloride (250 mg, 0.68 mmol) was added to the solution and the mixture was stirred for 18 h at rt. Water was added and the mixture was extracted 3× with EtOAc. The organic phase was washed with brine, dried over $Na_2SO_4$, filtered and concentrated under reduced pressure. The product was purified on a $SiO_2$ column, eluting with a gradient (0% MeOH/50% EtOAc/50% heptane→0% MeOH/100% EtOAc/0% heptane→15% MeOH/85% EtOAc/0% heptane), then on a C-18 column, eluting with a gradient of MeOH and water (0 to 100% MeOH), yielding 170 mg (46%) of the title compound.

$^1$H NMR (300 MHz, $CDCl_3$): ppm 1.44 (s, 9H), 1.73-1.91 (m, 3H), 2.10-2.19 (m, 1H), 3.10-3.40 (m, 3H), 3.45-3.61

(m, 2H), 4.27-4.35 (m, 1H), 4.50-4.56 (m, 1H), 4.60-4.69 (m, 1H), 5.17-5.41 (m, 3H), 6.93-7.03 (m, 2H), 7.06-7.32 (m, 9H), 7.47-7.56 (m, 1H), 7.82 (d, 1H), 8.48 (d, 1H).

Step B 2-((S)-2-((S)-1-((S)-2-Ammonio-3-phenylpropanoyl)pyrrolidine-2-carboxamido)-2-phenylethyl)pyridinium dichloride

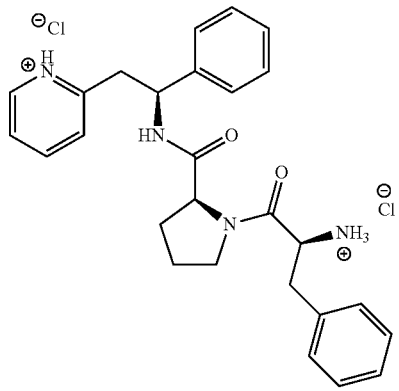

tert-Butyl (S)-1-oxo-3-phenyl-1-((S)-2-((S)-1-phenyl-2-(pyridin-2-yl)ethylcarbamoyl)pyrrolidin-1-yl)propan-2-ylcarbamate (170 mg, 0.31 mmol) was dissolved in a 1 M HCl solution in Et$_2$O (12.5 mL, 12.53 mmol). The reaction mixture was stirred at rt for 18 hours. The product was triturated in Et$_2$O. The solid was recovered by filtration on a Büchner funnel, washed with Et$_2$O and dried under vacuum. The solid was dissolved in water and freeze dried to afford 150 mg (93%) of the title compound.

$^1$H NMR (300 MHz, D$_2$O): ppm 1.39-1.48 (m, 1H), 1.58-1.65 (m, 2H), 1.92-1.99 (m, 1H), 2.66-2.74 (m, 1H), 2.95-3.10 (m, 2H), 3.29-3.45 (m, 3H), 4.15-4.27 (m, 2H), 5.09 (t, 1H), 6.97-7.17 (m, 10H), 7.59-7.64 (m, 2H), 8.18 (t, 1H), 8.35 (d, 1H);
[M+H]$^+$=443.3,
[M+Na]$^+$=465.2.

Example 11

(S)-1-((S)-2-Amino-4-methylpentanonyl)-N—((S)-1-phenyl-2-(pyridin-2-yl)ethyl)pyrrolidine-2-carboxamide

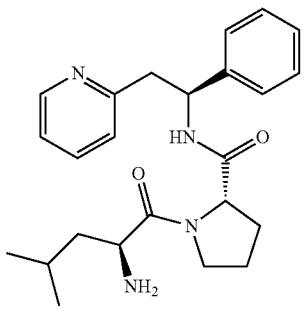 [SMILES: CC(C)C[C@H](N)C(=O)N1CCC[C@H]1C(=O)N[C@@H](Cc1ccccn1)c1ccccc1]

The title compound was prepared as the dichloride 2-[(2S)-2-{[(2S)-1-[(2S)-2-azaniumyl-4-methylpentanoyl]pyrrolidin-2-yl]formamido}-2-phenylethyl]pyridin-1-ium dichloride Step A tert-Butyl (S)-4-methyl-1-oxo-1-((S)-2-((S)-1-phenyl-2-(pyridin-2-yl)ethylcarbamoyl)pyrrolidin-1-yl)pentan-2-ylcarbamate

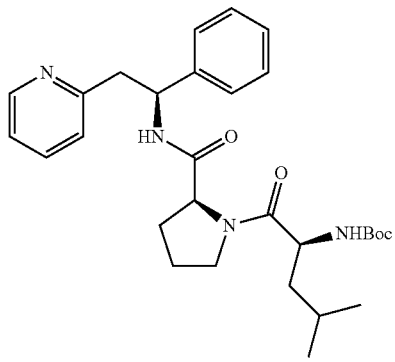 [SMILES: CC(C)C[C@H](NC(=O)OC(C)(C)C)C(=O)N1CCC[C@H]1C(=O)N[C@@H](Cc1ccccn1)c1ccccc1]

N-(tert-Butoxycarbonyl)-L-leucine (157 mg, 0.68 mmol) was dissolved in anhydrous DMF (4 mL). HATU (271 mg, 0.71 mmol) and DIPEA (0.39 mL, 2.24 mmol) were added and the mixture was stirred at rt for 30 minutes. Then, (2S)-2-{[(1S)-1-phenyl-2-(pyridin-1-ium-2-yl)ethyl]carbamoyl}pyrrolidin-1-ium dichloride (250 mg, 0.68 mmol) was added to the solution and the mixture was stirred for 18 hours at rt. Water was added and the mixture was extracted 3× with EtOAc. The organic phase was washed with brine, dried over Na$_2$SO$_4$, filtered and concentrated under reduced pressure. The product was purified on a SiO$_2$ column, eluting with a gradient (0% MeOH/50% EtOAc/50% heptane→0% MeOH/100% EtOAc/0% heptane→15% MeOH/85% EtOAc/0% heptane) then on a C-18 column, eluting with a gradient of MeOH and water (0 to 100% MeOH), yielding 200 mg (58%) of the title compound.

$^1$H NMR (300 MHz, CDCl$_3$): ppm 0.91 (d, 3H), 0.98 (d, 3H), 1.34-1.52 (m, 1H), 1.41 (s, 9H), 1.70-1.84 (m, 2H), 1.85-1.96 (m, 3H), 2.11-2.18 (m, 1H), 3.07-3.27 (m, 2H), 3.47-3.56 (m, 1H), 3.61-3.71 (m, 1H), 4.43-4.56 (m, 2H), 5.14-5.18 (m, 1H), 5.26-5.34 (m, 1H), 6.98 (d, J=7.7 Hz, 1H), 7.08-7.25 (m, 5H), 7.52 (t, 1H), 7.83 (d, 1H), 8.48 (d, 1H).

Step B 2-((S)-2-((S)-1-((S)-2-Ammonio-4-methylpentanoyl)pyrrolidine-2-carboxamido)-2-phenylethyl)pyridinium dichloride

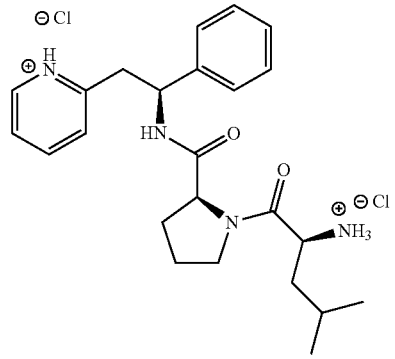

tert-Butyl (S)-4-methyl-1-oxo-1-((S)-2-((S)-1-phenyl-2-(pyridin-2-yl)ethylcarbamoyl)pyrrolidin-1-yl)pentan-2-yl-carbamate (200 mg, 0.39 mmol) was dissolved in a 1 M HCl solution in Et₂O (15.7 mL, 15.7 mmol). The reaction was stirred at rt for 18 h. The product was triturated in Et₂O. The solid was recovered by filtration on a Büchner funnel, washed with Et₂O and dried under vacuum. The solid was dissolved in water and freeze dried to afford 130 mg (69%) of the title compound.

¹H NMR (300 MHz, D₂O): ppm 0.72 (d, 6H), 1.31-1.49 (m, 4H), 1.65-1.74 (m, 2H), 1.93-2.02 (m, 1H), 3.23-3.49 (m, 4H), 3.99-4.04 (m, 1H), 4.16-4.21 (m, 1H), 5.07 (t, 1H), 7.08-7.20 (m, 5H), 7.63-7.67 (m, 2H), 8.22 (td, 1H), 8.37 (dd, 1H);

[M+H]⁺=409.2,
[M+Na]⁺=431.2.

Example 12

2-[(2 S)-2-{[(2 S)-1-[(2 S)-2-Azaniumyl-5-{[azaniumyl(iminiumyl)methyl]amino}pentanoyl]-pyrrolidin-2-yl]formamido}-2-phenylethyl]pyridin-1-ium tetrachloride

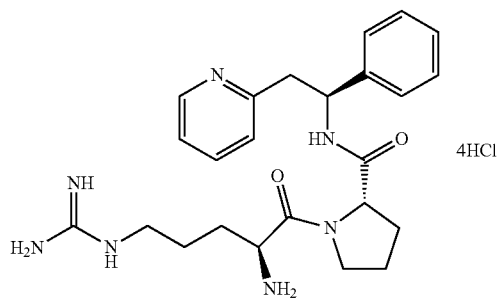 [SMILES: N=C(N)NCCC[C@H](N)C(=O)N1CCC[C@H]1C(=O)N[C@@H](Cc1ccccn1)c1ccccc1]

Step A tert-Butyl N-[(1Z)-{[(4S)-4-{[(tert-butoxy)carbonyl]amino}-5-oxo-5-[(2S)-2-{[(1 S)-1-phenyl-2-(pyridin-2-yl)ethyl]carbamoyl}pyrrolidin-1-yl]pentyl]amino}({[(tert-butoxy)carbonyl]imino})methyl]carbamate

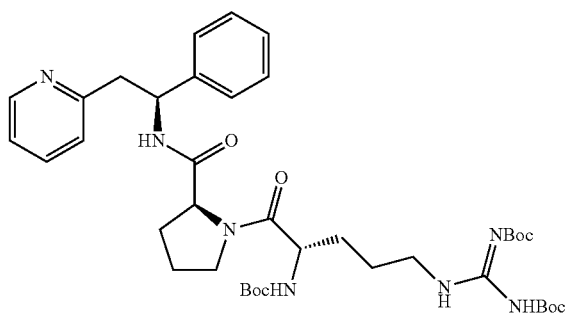

Boc-Arg(Boc)₂-OH (644 mg, 1.36 mmol) was dissolved in anhydrous DMF (7 mL). HATU (542 mg, 1.43 mmol) and DIPEA (0.78 mL, 4.48 mmol) were added and the mixture was stirred at rt for 30 minutes. Then, (2S)-2-{[(1S)-1-phenyl-2-(pyridin-1-ium-2-yl)ethyl]carbamoyl}pyrrolidin-1-ium dichloride (500 mg, 1.36 mmol) was added to the solution and the mixture was stirred for 18 h at rt. Water was added and the mixture was extracted 3× with EtOAc. The organic phase was washed with brine, dried over Na₂SO₄, filtered and concentrated under reduced pressure. The product was purified on a SiO₂ column, eluting with a gradient (0% MeOH/50% EtOAc/50% heptane→0% MeOH/100% EtOAc/0% heptane→10% MeOH/90% EtOAc/0% heptane) then on a C-18 column, eluting with a gradient of MeOH and water (0 to 100% MeOH), yielding 200 mg (20%) of the title compound.

¹H NMR (300 MHz, CDCl₃): ppm 1.43 (s, 9H), 1.46 (s, 9H), 1.51 (s, 9H), 1.57-1.76 (m, 4H), 1.86-1.99 (m, 3H), 2.12-2.25 (m, 1H), 3.11 (dd, 1H), 3.23-3.30 (m, 1H), 3.58-3.95 (m, 4H), 4.42 (t, 1H), 4.56 (d, 1H), 5.31-5.38 (m, 2H), 6.98 (d, 1H), 7.17-7.33 (m, 5H), 7.54 (t, 1H), 7.93 (d, 1H), 8.56 (d, 1H).

Step B

2-[(2S)-2-{[(2S)-1-[(2S)-2-Azaniumyl-5-{[azaniumyl(iminiumyl)methyl]amino}pentanoyl]pyrrolidin-2-yl]formamido}-2-phenylethyl]pyridin-1-ium tetrachloride

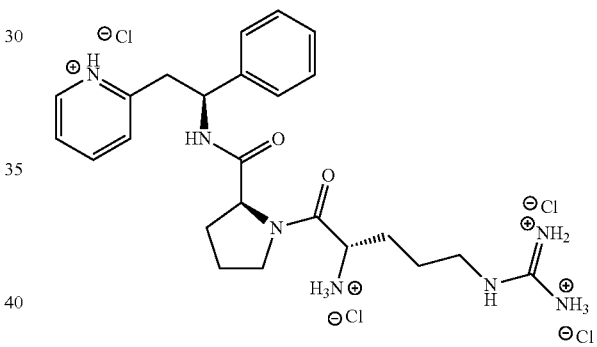

tert-Butyl N-[(1Z)-{[(4S)-4-{[(tert-butoxy)carbonyl]amino}-5-oxo-5-[(2S)-2-{[(1S)-1-phenyl-2-(pyridin-2-yl)ethyl]carbamoyl}pyrrolidin-1-yl]pentyl]amino}({[(tert-butoxy)carbonyl]imino})methyl]carbamate (200 mg, 0.27 mmol) was dissolved in a 1 M HCl solution in Et₂O (5.3 mL, 10.64 mmol). The reaction was stirred at rt for 18 hours. The product was triturated in Et₂O. The solid was recovered by filtration on a Buchner funnel, washed with Et₂O and dried under vacuum. The solid was dissolved in water and freeze dried to afford 140 mg (88%) of the title compound.

¹H NMR (300 MHz, D₂O): ppm 1.31-1.57 (m, 3H), 1.66-1.78 (m, 4H), 2.00-2.10 (m, 1H), 2.99 (t, 2H), 3.28-3.40 (m, 4H), 4.16 (t, 1H), 4.26 (t, 1H), 5.09 (t, 1H), 7.10-7.13 (m, 2H), 7.16-7.21 (m, 3H), 7.67-7.71 (m, 2H), 8.27 (t, 1H), 8.40 (d, 1H);

[M+H]⁺=452.2.

Biological Activity

Prodrugs described herein are contemplated to be administered orally by those suffering with depression or pain.

Example 13

This example illustrates that different prodrugs of (S)-1-phenyl-2-(pyridin-2-yl)ethanamine, wherein R1 is $C_{1-6}$ alkylC(O)O($C_{1-6}$ alkoxy), may be used to achieve differing rates of conversion (i.e., slow or rapid) to (S)-1-phenyl-2-(pyridin-2-yl)ethanamine to ascertain a suitable PK profile. Hence, varying R1 to produce different prodrugs results in different pharmacokinetic profiles of (S)-1-phenyl-2-(pyridin-2-yl)ethanamine. Further, this Example illustrates that there is no expected loss in oral exposure when a prodrug is converted to free base. Conversion of a prodrug wherein R1 is $C_{1-6}$ alkylC(O)O($C_{1-6}$ alkoxy) to (S)-1-phenyl-2-(pyridin-2-yl)ethanamine is expected to occur via an initial enzymatic hydrolysis of a functional group, such as an ester, followed by a spontaneous conversion to (S)-1-phenyl-2-(pyridin-2-yl)ethanamine. Enzymes involved are expected to be several non-specific, high capacity esterases, which can be shown by inhibiting the conversion with a non-selective esterase inhibitor but not inhibiting the conversion using selective inhibitors. Such esterases are expected to be distributed throughout the human body. Human Intestinal Fluid (HIF), human liver S9 fraction and human whole blood have been used to examine the pharmacokinetic properties of the prodrugs of (S)-1-phenyl-2-(pyridin-2-yl)ethanamine as well as the formation rate and formation extent of the (S)-1-phenyl-2-(pyridin-2-yl)ethanamine in different bodily compartments. The formation rate of (S)-1-phenyl-2-(pyridin-2-yl)ethanamine from different prodrugs of (S)-1-phenyl-2-(pyridin-2-yl)ethanamine differs markedly in all tested assays, as shown in Table 1.

TABLE 1

| Example Compound | HIF Assay | | Hum Liver Assay | | Hum Blood Assay | |
|---|---|---|---|---|---|---|
| | Formation Rate HIF ($k^{-1}$) | Formation extent HIF (%) | Prodrug Clint Hum Liver S9 (ml/min/mg) | Formation extent Hum Liver S9 (%) | Formation Rate Hum Blood ($k^{-1}$) | Formation extent Hum Blood (%) |
| Example 1 | 8.4 | 100 | 2300 | 100 | 45 | 100 |
| Example 2 Diastereomer 1 | 11 | 99 | 1700 | 96 | 0.4 | 76 |
| Example 2 Diastereomer 2 | 0.5 | 100 | 1900 | 92 | 0.2 | 71 |
| Example 3 Diastereomer 1 | 0.3 | 100 | 240 | 96 | Not Measured | Not Measured |
| Example 3 Diastereomer 2 | 8.9 | 100 | 1600 | 94 | 1.2 | 100 |
| Example 4 Diastereomer 1 | 2.4 | 72 | 1200 | 57 | Not measured | Not Measured |
| Example 4 Diastereomer 2 | 7.5 | 93 | 1900 | 52 | 2.6 | 100 |

The in vitro results shown in Table 1 show that different pharmacokinetic plasma profiles of (S)-1-phenyl-2-(pyridin-2-yl)ethanamine can be achieved by using different prodrugs of (S)-1-phenyl-2-(pyridin-2-yl)ethanamine. Hence, selection of a particular prodrug will allow different pharmacokinetic profiles of (S)-1-phenyl-2-(pyridin-2-yl)ethanamine to be achieved, that is, different prodrugs may be used to achieve a slow or rapid conversion to (S)-1-phenyl-2-(pyridin-2-yl)ethanamine. Human Intestinal Fluids (HIF), Human Liver and Human Blood assays used to generate the results shown in Table 1 have been described in Malmborg J & Ploeger B A, J. Pharmacol Toxicol Methods (2013) May-June 67(3) 203-13, which is incorporated by reference herein.

Example 14

This example illustrates that different prodrugs of (S)-1-phenyl-2-(pyridin-2-yl)ethanamine, wherein R1 is

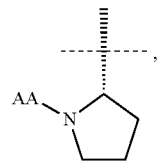

may be used to achieve differing rates of conversion (i.e., slow or rapid) to (S)-1-phenyl-2-(pyridin-2-yl)ethanamine to ascertain a suitable PK profile. Hence, varying R1 to produce different prodrugs results in different pharmacokinetic profiles of (S)-1-phenyl-2-(pyridin-2-yl)ethanamine. Further, this Example illustrates that there is no expected loss in oral exposure when a prodrug is converted to free base.

Conversion of a prodrug to (S)-1-phenyl-2-(pyridin-2-yl)ethanamine of a compound of formula (I) wherein R1 is:

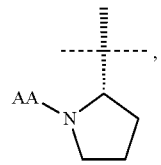

is expected to occur via enzymatic hydrolysis at the proline C-terminus, releasing a dipeptide and (S)-1-phenyl-2-(pyridin-2-yl)ethanamine. The enzyme involved is expected to be dipeptidyl peptidase IV (DPPIV), which can be shown by inhibiting the conversion with a selective inhibitor of this enzyme. DPPIV is expected to be distributed throughout the human body. Human Intestinal Fluid (HIF), human liver S9 fraction and human whole blood have been used to examine the pharmacokinetic properties of prodrugs of (S)-1-phenyl-2-(pyridin-2-yl)ethanamine as well as the formation rate and formation extent of the (S)-1-phenyl-2-(pyridin-2-yl)ethanamine in different bodily compartments. Caco-2 cells have been used to evaluate the permeability and absorption potential of the prodrugs of (S)-1-phenyl-2-(pyridin-2-yl)ethanamine. The formation rate of (S)-1-phenyl-2-(pyridin-2-yl)ethanamine from different prodrugs of (S)-1-phenyl-2-(pyridin-2-yl)ethanamine differed in the tested assays, especially in human blood, as shown in Table 2. The differing permeability displayed by different prodrugs of (S)-1-phenyl-2-(pyridin-2-yl)ethanamine suggests that the systemic exposure of prodrug of (S)-1-phenyl-2-(pyridin-2-yl)ethanamine will vary depending on prodrug chosen.

identifying prodrugs with appropriate pharmacokinetic profiles in man, multi-compartmental, physiologically-based pharmacokinetic models (PBPK) were constructed for both (S)-1-phenyl-2-(pyridin-2-yl)ethanamine and each prodrug under consideration. The PBPK models were validated using a set of known prodrugs for which human PK data was available (see Malmborg J & Ploeger B A, J. Pharmacol Toxicol Methods (2013) May-June 67(3) 203-13, which is incorporated herein by reference). Rate constants used in the model were based on in vitro stability studies (i.e. human intestinal fluid, human blood, etc.) conducted with both prodrugs and (S)-1-phenyl-2-(pyridin-2-yl)ethanamine (example values shown in Tables 1 and 2).

Table 3 shows key pharmacokinetic predictions for Example 5—one of the DPPIV cleaved prodrugs. As exemplified in Table 3 Cmax exposure of (S)-1-phenyl-2-(pyri-

TABLE 2

| | HIF Assay | | Hum Liver Assay | | Hum Blood Assay | | Caco-2 |
|---|---|---|---|---|---|---|---|
| Example | Formation Rate HIF ($k^{-1}$) | Formation extent HIF (%) | Prodrug Clint Hum Liver S9 (ml/min/mg) | Formation extent Hum Liver S9 (%) | Formation Rate Hum Blood ($k^{-1}$) | Formation extent Hum Blood (%) | Caco-2 Papp ($10^{-6}$ cm/s) |
| 5 | 4.1 | 88 | 120 | 87 | 6.5 | 93 | 1.4 |
| 6 | 2.7 | 72 | 73 | 88 | 4.5 | 90 | 0.07 |
| 7 | 2.3 | 86 | 33 | 83 | 1.1 | 59 | 1.6 |
| 8 | 2.6 | 97 | 51 | 94 | 1.1 | 86 | 3.2 |
| 12 | 3.8 | 87 | 69 | 100 | 8.9 | 93 | 8.6 |

The in vitro assays show that different pharmacokinetic plasma profiles of (S)-1-phenyl-2-(pyridin-2-yl)ethanamine can be achieved by using different prodrugs. Hence, different pharmacokinetic profiles of (S)-1-phenyl-2-(pyridin-2-yl)ethanamine can be achieved by use of different prodrugs.

Example 15

This example illustrates that oral doses of prodrug of (S)-1-phenyl-2-(pyridin-2-yl)ethanamine have a similar pharmacokinetic profile to an IV 1-hour infusion of (S)-1-phenyl-2-(pyridin-2-yl)ethanamine.

Based on in vitro data, (S)-1-phenyl-2-(pyridin-2-yl)ethanamine (lanicemine) projects to have good oral bioavailability (>75%) in man, but a higher than acceptable Cmax when given as an intravenous bolus (relative to its safety profile as a 1-hr infusion). One selection criterion used to evaluate the utility and suitability of a prodrug of (S)-1-phenyl-2-(pyridin-2-yl)ethanamine was the potential for the prodrug to preserve (S)-1-phenyl-2-(pyridin-2-yl)ethanamine's oral/1-hr iv infusion characteristics (e.g., $T_{max}$, $C_{max}$, AUC) while blunting the $C_{max}$ of the active moiety when the prodrug is administered directly into the blood stream thereby attenuating potential misuse (e.g. abuse liability) and/or Cmax driven safety concerns. As a means of din-2-yl)ethanamine is predicted to increase by >2× when a given oral dose form is crushed and illicitly delivered as a bolus i.v. administration. In contrast, (S)-1-phenyl-2-(pyridin-2-yl)ethanamine released from an oral administered prodrug has a PK profile similar to a 1-hr infusion of (S)-1-phenyl-2-(pyridin-2-yl)ethanamine with no Cmax doubling when given as a bolus i.v. Furthermore, because conversion to (S)-1-phenyl-2-(pyridin-2-yl)ethanamine is driven selectively by DPPIV, a DPPIV inhibitor can be used to stop conversion in case of purposeful or inadvertent misuse—an added safety feature embedded within the DPPIV prodrug design.

In Table 3 Compound 1 is (S)-1-phenyl-2-(pyridin-2-yl)ethanamine. In Table 3 all doses are selected to contain equivalent amounts of Compound 1 [(S)-1-phenyl-2-(pyridin-2-yl)ethanamine free base], i.e. each dose contains the same amount of Compound 1 within it and potentially available for release in the form of free base (S)-1-phenyl-2-(pyridin-2-yl)ethanamine. Thus, modeled Cmax concentrations of free base Compound 1 may be compared directly across different administrations of (S)-1-phenyl-2-(pyridin-2-yl)ethanamine and prodrug of (S)-1-phenyl-2-(pyridin-2-yl)ethanamine, as shown within Table 3.

TABLE 3

| | Compound 1 (IV 1-h infusion) Model Predictions | Compound 1 (IV-Bolus) Model Predictions | Compound 1 from Prodrug (IV-Bolus) Model Predictions | Compound 1 (Oral) Model Predictions | Compound 1 from Prodrug (Oral) Model Predictions |
|---|---|---|---|---|---|
| Dose | 100 mg | 114 mg | 270 mg | 114 mg | 270 mg |
| Tmax | 1 h | 0.11 h | 0.47 h | 0.88 h | 1.1 h |

TABLE 3-continued

|  | Compound 1 (IV 1-h infusion) Model Predictions | Compound 1 (IV-Bolus) Model Predictions | Compound 1 from Prodrug (IV-Bolus) Model Predictions | Compound 1 (Oral) Model Predictions | Compound 1 from Prodrug (Oral) Model Predictions |
|---|---|---|---|---|---|
| Cmax | 825 ng/ml | 1821 ng/ml | 825 ng/ml | 825 ng/ml | 825 ng/ml |
| AUC | 7590 | 8723 | 9089 | 6967 | 8251 |

Example 16

This example illustrates that when doses of prodrug of (S)-1-phenyl-2-(pyridin-2-yl)ethanamine dihydrochloride (Example 5) and (S)-1-phenyl-2-(pyridin-2-yl)ethanamine dihydrochloride were administered to dogs, the risk of seizures, as represented by NOEL and LOEL, was less with the prodrug.

(S)-1-phenyl-2-(pyridin-2-yl)ethanamine dihydrochloride and vehicle were administered once per day via oral gavage (water). Formulations were prepared twice, once weekly. Dosing formulations were stored and refrigerated (2-8° C.) in amber glass containers until required for dosing. A range of concentrations of (S)-1-phenyl-2-(pyridin-2-yl)ethanamine dihydrochloride in vehicle were prepared in order to keep the dose volume for all doses (1 mL/kg). Individual doses were based on the most recent body weights of dogs used in the study.

A prodrug of (S)-1-phenyl-2-(pyridin-2-yl)ethanamine as fumarate salt (example 5) and vehicle were administered once per day for 14 days via oral gavage at approximately the same time each day (±1 hour), (vehicle is 0.3 M gluconic acid pH 3.0). A range of concentrations of prodrug of (S)-1-phenyl-2-(pyridin-2-yl)ethanamine as fumarate salt in vehicle were prepared (for example 3, 10 and 30 mg/mL of prodrug of (S)-1-phenyl-2-(pyridin-2-yl)ethanamine) in order to keep the dose volume for all doses (2 mL/kg). The dosing formulations were warmed to room temperature by stirring for at least 30 minutes prior to dosing and continuously throughout the administration procedure. Individual doses were based on the most recent body weights of dogs used in the study.

Table 4 Compound 1 is (S)-1-phenyl-2-(pyridin-2-yl)ethanamine. Table 4 illustrates the highest blood levels in which seizures do not occur (No Observed Effect Limit, NOEL), and the lowest blood levels in which seizures occur (Lowest Observed Effect Limit, LOEL), following administration of Compound 1 dihydrochloride and following administration of a fumarate salt prodrug of Compound 1. In each case the highest blood concentration (Cmax) of free base (S)-1-phenyl-2-(pyridin-2-yl)ethanamine is measured. In the first case, the free base (S)-1-phenyl-2-(pyridin-2-yl)ethanamine is generated directly from Compound 1, administered as the dihydrochloride salt. In the second case, the free base (S)-1-phenyl-2-(pyridin-2-yl)ethanamine is generated via in vivo conversion from a prodrug of Compound 1, administered as the fumarate salt. The NOEL for seizures was higher when the prodrug of (S)-1-phenyl-2-(pyridin-2-yl)ethanamine as fumarate salt was administered compared to when (S)-1-phenyl-2-(pyridin-2-yl)ethanamine as dihydrochloride salt was administered.

TABLE 4

| Treatment Administered | NOEL Seizures in dog Compound 1 Cmax (Dose administered)* | LOEL Seizures in dog Compound 1 Cmax (Dose administered)* |
|---|---|---|
| Compound 1, as di-HCl salt | 3-6 uM (10 mg/kg) | 6-8 uM (20 mg/kg) |
| Prodrug of Compound 1, as fumarate salt | 10 uM (20 mg/kg) | 20-36 uM (60 mg/kg) |

*All doses administered (in parentheses) reflect free base concentration.

Example 17

Figure 1B:
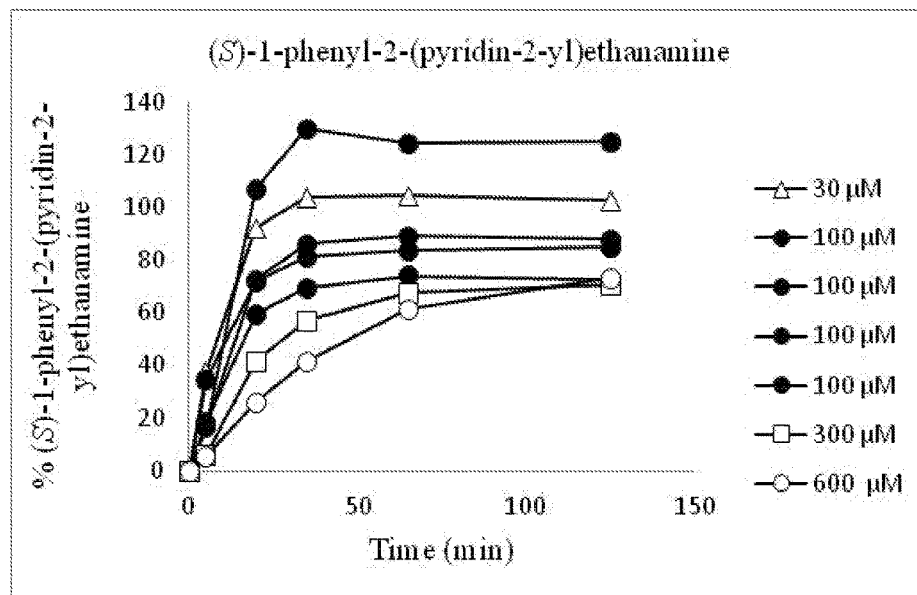

This example illustrates that increasing doses of prodrug of (S)-1-phenyl-2-(pyridin-2-yl)ethanamine, Example 5, produces less than proportional increases in the concentration of (S)-1-phenyl-2-(pyridin-2-yl)ethanamine in human intestinal fluid, as illustrated in FIG. 1a and FIG. 1b. As a consequence, it makes it harder to get high concentrations of (S)-1-phenyl-2-(pyridin-2-yl)ethanamine from administering a prodrug of (S)-1-phenyl-2-(pyridin-2-yl)ethanamine relative to administering (S)-1-phenyl-2-(pyridin-2-yl)ethanamine directly, which is sought after for drug abuse. Without wishing to be bound by theory, prodrugs of (S)-1-phenyl-2-(pyridin-2-yl)ethanamine, wherein R1 is, are primarily cleaved by DPPIV. There is the potential for endogenous and/or exogenous modulation of DPPIV to impact the conversion of the prodrug to (S)-1-phenyl-2-(pyridin-2-yl)ethanamine.

Stock solutions of prodrug of (S)-1-phenyl-2-(pyridin-2-yl)ethanamine (0.33, 1, 3 and 6 mmol/L) were prepared by adding a volume (8.25, 25, 75 and 150 µL) of 20 mmol/L solution of prodrug of (S)-1-phenyl-2-(pyridin-2-yl)ethanamine dissolved in DMSO, to FaSSIF-v2 (491.75, 475, 425 and 350 µL). Subsequently, 10 µL of prodrug of (S)-1-phenyl-2-(pyridin-2-yl)ethanamine stock solution was added to supernatant (90 µL HIF) in a glass vial, mixed for 1 min, and injected on the LC-UV system. The initial concentration in the incubations were 33, 100, 300 and 600 µmol/L and samples were taken at 5, 20, 35, 65 and 125 min from the start of the incubation. An incubation experiment with (S)-1-phenyl-2-(pyridin-2-yl)ethanamine µmol/L) was used as the standard sample (one-point-calibration) to determine the formation rate and concentration of (S)-1-phenyl-2-(pyridin-2-yl)ethanamine. Analysis was performed on a photodiode array detector (the analytical wavelength used was 261 nm) coupled to a Waters Acquity UPLC. The column used was a BEH C-18, 1.7 µm, 2.1×50 mm ID held at 40° C. and using a 0.2 jam in-line pre-filter. The mobile phases used consisted of A: 0.03% TFA in H2O (v/v) and B: 0.03% TFA in acetonitrile (v/v). Example gradient: The initial 1% B was ramped to 95% B over 7 min and then kept at 95% B for 0.4 min at a flow rate of 0.6 mL/min. The conversion rate from prodrug to (S)-1-phenyl-2-(pyridin-2- yl)ethanamine was determined by fitting the measured prodrug and (S)-1-phenyl-2-(pyridin-2-yl)ethanamine concentrations versus time.

Example 18

Consistent with the in vitro observations from Example 17, in vivo studies (Example 18 below) in rats illustrate that Cmax exposures of (S)-1-phenyl-2-(pyridin-2-yl)ethanamine, as described above, increases less than proportionally upon the transition between therapeutic and supra-therapeutic doses of a prodrug of (S)-1-phenyl-2-(pyridin-2-yl)ethanamine. The results of these in vivo studies are tabulated in Table 5.

52 male and 52 female rats were administered either (a) prodrug of (S)-1-phenyl-2-(pyridin-2-yl)ethanamine as a fumarate salt in vehicle (0.3M Gluconic Acid, pH 3.0) or (b) vehicle (0.3M Gluconic Acid, pH 3.0) once per day for 14 days at approximately the same time each day (09:26+/−124 minutes). The doses (30, 100, and 300 mg/kg of prodrug of (S)-1-phenyl-2-(pyridin-2-yl)ethanamine) were administered in a dose volume of 10 mL/kg. After 14 days, blood samples were collected 24 hours post-dose from lateral tail vein in restrained animals. Blood samples were collected using 50 ul neutral Sarstedt Minivette POCT capillary tubes. The blood was then transferred to pre-chilled tubes containing ice cold sodium citrate, shaken 5-10 times by hand and frozen in dry ice within 10 seconds of collection. Whole blood samples were shipped frozen on dry ice to Covance Laboratories Inc. for analysis. Samples were analyzed for concentrations of prodrug of (S)-1-phenyl-2-(pyridin-2-yl)ethanamine and (S)-1-phenyl-2-(pyridin-2-yl)ethanamine. All analytical work was conducted by Covance Laboratories, Inc., Madison, Wis. using an LC/MS/MS analytical method developed and validated by that laboratory.

Table 5 illustrates toxicokinetic parameters following administering therapeutic and supra-therapeutic doses of prodrug of (S)-1-phenyl-2-(pyridin-2-yl)ethanamine to rats.

TABLE 5

Mean Toxicokinetic Parameters for (S)-1-Phenyl-2-(pyridin-2-yl)ethanamine in Rats after Oral Administration of (S)-1-((S)-2-Amino-3-methylbutanoyl)-N-((S)-1-phenyl-2-(pyridin-2-yl)ethyl)pyrrolidine-2-carboxamide fumarate (Example 5) for 14 Days

| (S)-1-Phenyl-2-(pyridin-2-yl)ethanamine - Male (Day 14) | | | |
|---|---|---|---|
| Dose | 30 mg/kg/day (75 μmol/kg/day) | 100 mg/kg/day (250 μmol/kg/day) | 300 mg/kg/day (750 μmol/kg/day) |
| $C_{max}$ (nmol/L) | 9980 ± 890 | 20700 ± 7660 | 50700 ± 18700 |
| $AUC_{0-t}$ (nmol · hr/L) | 133000 ± 11100 | 305000 ± 96600 | 784000 ± 180000 |
| $T_{max}$ (hours) | 3.33 ± 2.52 | 3.00 ± 0 | 1.54 ± 1.27 |

| (S)-1-Phenyl-2-(pyridin-2-yl)ethanamine - Female (Day 14) | | | |
|---|---|---|---|
| Dose | 30 mg/kg/day (75 μmol/kg/day) | 100 mg/kg/day (250 μmol/kg/day) | 300 mg/kg/day (750 μmol/kg/day) |
| $C_{max}$ (nmol/L) | 11900 ± 1990 | 32400 ± 2750 | 83800 ± 8810 |
| $AUC_{0-t}$ (nmol · hr/L) | 14600 ± 10000 | 402000 ± 14000 | 1150000 ± 319000 |
| $T_{max}$ (hours) | 3.00 ± 0 | 1.67 ± 1.15 | 2.67 ± 2.89 |

The invention claimed is:

1. A compound of formula (I):

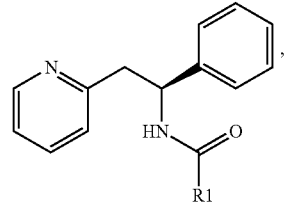

wherein R1 is $C_{1-6}$ alkylC(O)O($C_{1-6}$ alkoxy), or

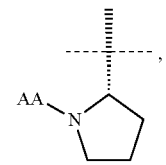

wherein AA is a peptide bond-linked natural amino acid; or a pharmaceutically acceptable salt thereof.

2. The compound according to claim 1, wherein the compound is selected from the group consisting of:
- (S)-(1-Phenyl-2-(pyridin-2-yl)ethylcarbamoyloxy)methyl isobutyrate;
- 2-Methyl-1-((S)-1-phenyl-2-(pyridin-2-yl)ethylcarbamoyloxy)propyl isobutyrate;
- 2-Methyl-1-((S)-1-phenyl-2-(pyridin-2-yl)ethylcarbamoyloxy)propyl isobutyrate diastereomer 1;
- 2-Methyl-1-((S)-1-phenyl-2-(pyridin-2-yl)ethylcarbamoyloxy)propyl isobutyrate diastereomer 2;
- 1-((S)-1-phenyl-2-(pyridin-2-yl)ethylcarbamoyloxy)ethyl acetate;
- 1-((S)-1-phenyl-2-(pyridin-2-yl)ethylcarbamoyloxy)ethyl acetate diastereomer 1;
- 1-((S)-1-phenyl-2-(pyridin-2-yl)ethylcarbamoyloxy)ethyl acetate diastereomer 2;
- 1-((S)-1-Phenyl-2-(pyridin-2-yl)ethylcarbamoyloxy)ethyl isobutyrate;
- 1-((S)-1-Phenyl-2-(pyridin-2-yl)ethylcarbamoyloxy)ethyl isobutyrate diastereomer 1;
- 1-((S)-1-Phenyl-2-(pyridin-2-yl)ethylcarbamoyloxy)ethyl isobutyrate diastereomer 2;
- (S)-1-((S)-2-Amino-3-methylbutanoyl)-N—((S)-1-phenyl-2-(pyridin-2-yl)ethyl)pyrrolidine-2-carboxamide;
- (S)-1-((S)-2,6-Diaminohexanoyl)-N—((S)-1-phenyl-2-(pyridin-2-yl)ethyl)pyrrolidine-2-carboxamide;
- (S)-1-((S)-2-Amino-3-(1H-imidazol-4-yl)propanoyl)-N—((S)-1-phenyl-2-(pyridin-2-yl)ethyl)pyrrolidine-2-carboxamide;
- 2-((S)-2-((S)-1-((S)-2-Amino-3-(4-hydroxyphenyl)propanoyl)pyrrolidine-2-carboxamido)-2-phenylethyl)pyridine;
- 2-((S)-2-((S)-1-((S)-2-Amino-3-(1H-indol-3-yl)propanoyl)pyrrolidine-2-carboxamido)-2-phenylethyl)pyridine;
- (S)-1-((S)-2-Amino-3-phenylpropanoyl)-N—((S)-1-phenyl-2-(pyridin-2-yl)ethyl)pyrrolidine-2-carboxamide; and
- (S)-1-((S)-2-Amino-4-methylpentanoyl)-N—((S)-1-phenyl-2-(pyridin-2-yl)ethyl)pyrrolidine-2-carboxamide;

or a pharmaceutically acceptable salt of any one of the foregoing.

3. A compound that is (S)-1-((S)-2-amino-3-methylbutanoyl)-N—((S)-1-phenyl-2-(pyridin-2-yl)ethyl)pyrrolidine-2-carboxamide,

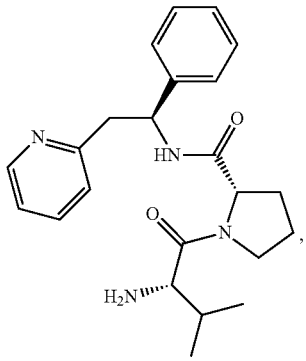 [SMILES: CC(C)[C@H](N)C(=O)N1CCC[C@H]1C(=O)N[C@@H](Cc1ccccn1)c1ccccc1]

or a pharmaceutically acceptable salt thereof.

4. A compound that is (S)-1-((S)-2-amino-3-methylbutanoyl)-N—((S)-1-phenyl-2-(pyridin-2-yl)ethyl)pyrrolidine-2-carboxamide dihydrochloride salt:

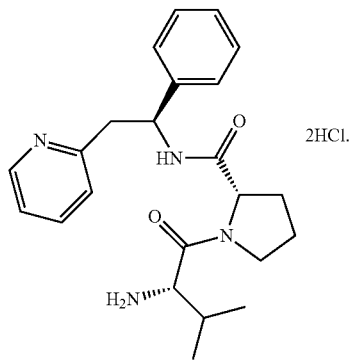 [SMILES: CC(C)[C@H](N)C(=O)N1CCC[C@H]1C(=O)N[C@@H](Cc1ccccn1)c1ccccc1]

5. A compound that is (S)-1-((S)-2-amino-3-methylbutanoyl)-N—((S)-1-phenyl-2-(pyridin-2-yl)ethyl)pyrrolidine-2-carboxamide fumarate salt:

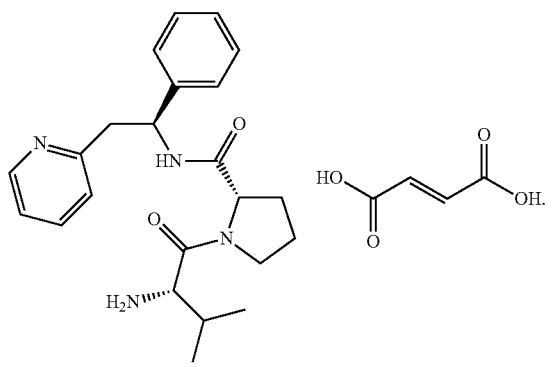

6. A pharmaceutical composition comprising a compound according to any one of claims 1-3, 4, and 5, or a pharmaceutically acceptable salt thereof, in association with a pharmaceutically acceptable adjuvant, diluent or carrier.

7. A method of treating depression which comprises administering to a patient in need thereof a therapeutically effective amount of a compound according to any one of claims 1-3, 4, and 5, or a pharmaceutically acceptable salt thereof.

8. The method according to claim 7, wherein the depression disorder is major depressive disorder.

9. A method of treating pain which comprises administering to a patient in need thereof a therapeutically effective amount of a compound according to according to any one of claims 1-3, 7, and 5, or a pharmaceutically acceptable salt thereof.

10. A method of treating Rett Syndrome, suicidal ideation, bipolar disorder, obsessive compulsive disorder, sarin gas poisoning, or status epilepticus, which comprises administering to a patient in need thereof a therapeutically effective amount of a compound according to any one of claims 1-3, 4, and 5, or a pharmaceutically acceptable salt thereof.

11. A compound that is (S)—N—((S)-1-phenyl-2-(pyridin-2-yl)ethyl)pyrrolidine-2-carboxamide:

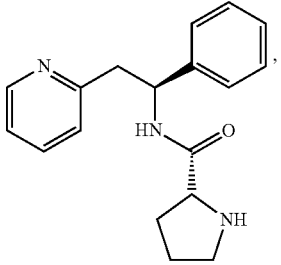

or a salt thereof.

12. A compound that is (S)—N—((S)-1-phenyl-2-(pyridin-2-yl)ethyl)pyrrolidine-2-carboxamide dihydrochloride:

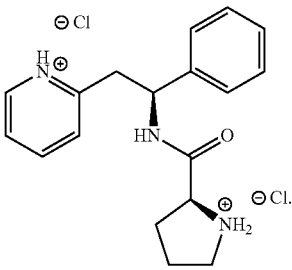

* * * * *